United States Patent [19]

Iida et al.

[11] Patent Number: 5,408,991
[45] Date of Patent: Apr. 25, 1995

[54] ENDOSCOPE SYSTEM WHEREIN CLEANING SOLUTION FLOWS AT SAME SPEED IN CLEANING SOLUTION SUPPLY SECTION AND IN ALL FLOW PATHS OF INTERNAL CONDUITS

[75] Inventors: Yoshihiro Iida; Koji Takamura, both of Tokyo; Shigeru Nakajima, Niiza; Jun Hiroya, Tokyo; Nobuyuki Nakanishi, Sagamihara; Takeaki Nakamura, Tokyo; Hiroyuki Sasa, Tokyo; Yoshisada Aoki, Tokyo; Osamu Tamada, Tokyo, all of Japan

[73] Assignee: Olympus Optical Co., Ltd., Tokyo, Japan

[21] Appl. No.: 99,825

[22] Filed: Jul. 29, 1993

[30] Foreign Application Priority Data

Jul. 31, 1992 [JP] Japan .................................. 4-205722
Aug. 24, 1992 [JP] Japan .................................. 4-224179
Mar. 31, 1993 [JP] Japan .................................. 5-074782

[51] Int. Cl.⁶ ........................... A61B 1/015; A61B 1/12
[52] U.S. Cl. ............................................ 128/4; 128/6; 134/22.12
[58] Field of Search ................... 128/4, 6; 134/166 C, 134/168 C, 169 C, 171, 167 C, 22.12, 22.18, 24

[56] References Cited

U.S. PATENT DOCUMENTS 4,525,220  6/1985  Sasa et al. .
4,526,622  7/1985  Takamura et al. .................. 134/21
4,526,623  7/1985  Ishii et al. .
4,576,650  3/1986  Yabe et al. .
4,579,597  4/1986  Sasa et al. .
4,579,598  4/1986  Sasa et al. .
4,637,378  1/1987  Sasa ...................................... 128/4
4,667,691  5/1987  Sasa .
4,748,970  6/1988  Nakajima .
4,777,529 10/1988  Nakajima et al. ................ 128/4 X
5,213,093  5/1993  Swindle .............................. 128/4

FOREIGN PATENT DOCUMENTS 64-26005  2/1989  Japan .

*Primary Examiner*—Richard J. Apley
*Assistant Examiner*—John Mulcahy
*Attorney, Agent, or Firm*—Frishauf, Holtz, Goodman & Woodward

[57] ABSTRACT

An endoscope system includes an endoscope having internal conduits, a cleaning solution supply portion formed in the endoscope and communicating with the internal conduits, and a solution feed unit for feeding a cleaning solution to the cleaning solution supply portion. The internal conduits are formed such that the cleaning solution supplied from the cleaning solution supply portion to the internal conduits by the solution feed unit flows in all the flow paths of the internal conduits at a flow speed almost equal to that in the cleaning solution supply portion.

22 Claims, 14 Drawing Sheets

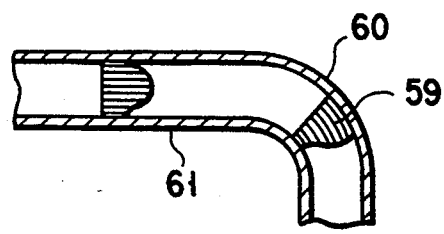
F I G. 11
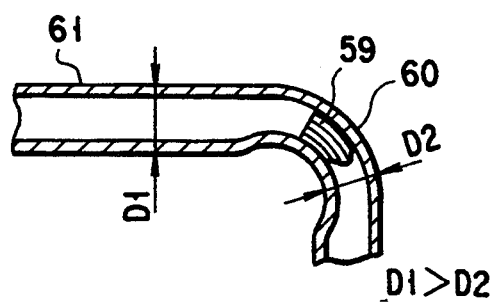
F I G. 12
F I G. 13
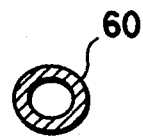
F I G. 14
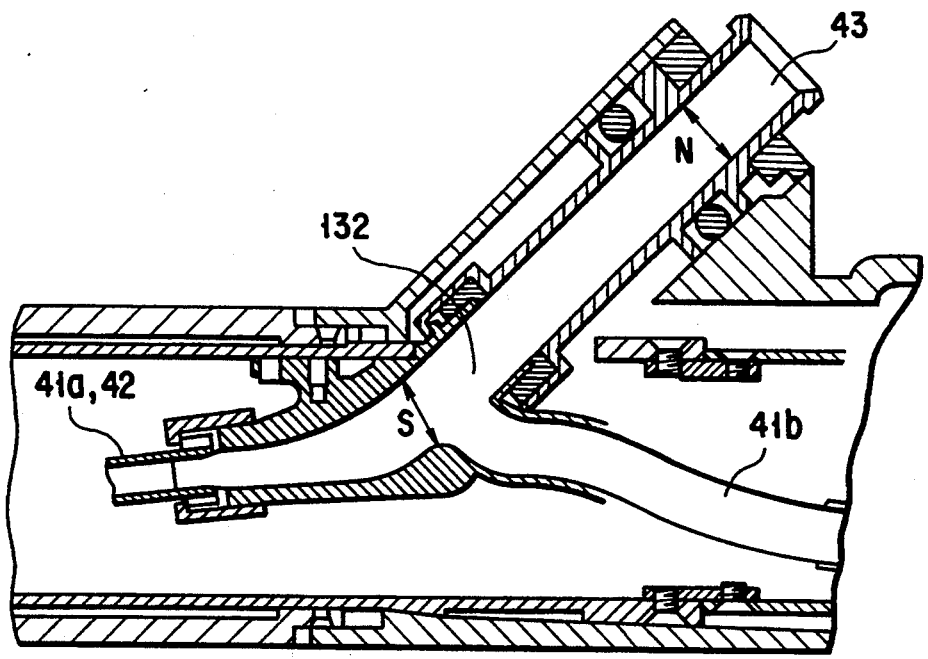
F I G. 15

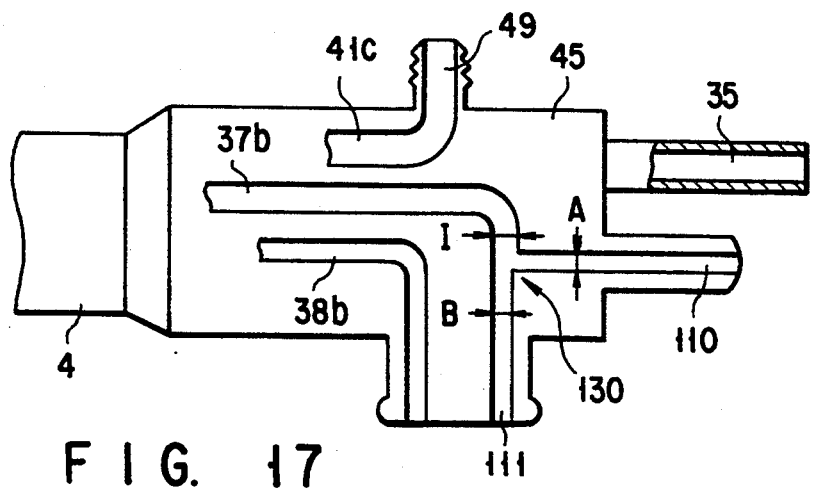
F I G. 17
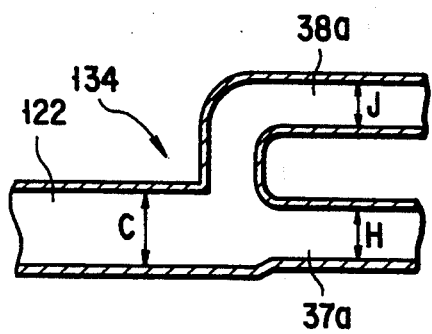
F I G. 18
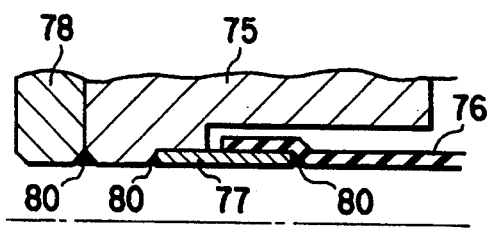
F I G. 19
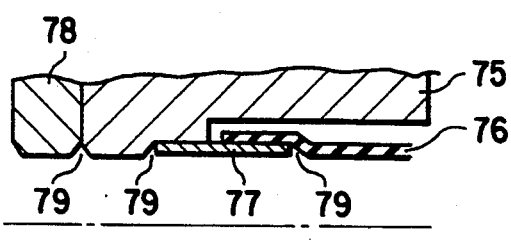
F I G. 20
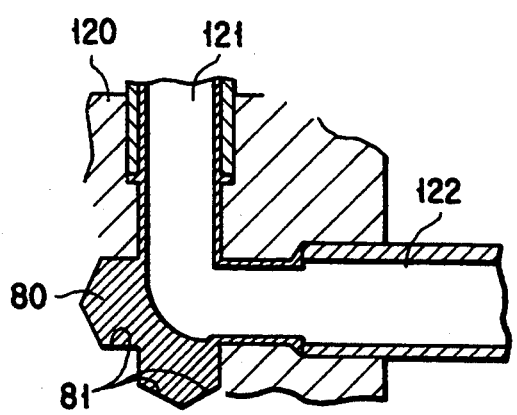
F I G. 21

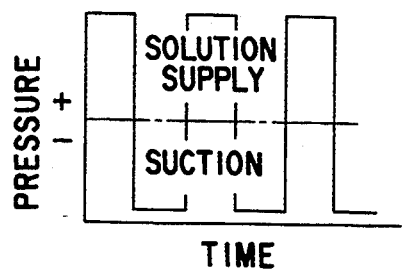
F I G. 25
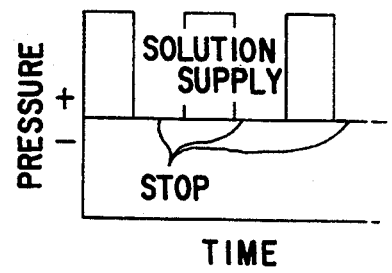
F I G. 26
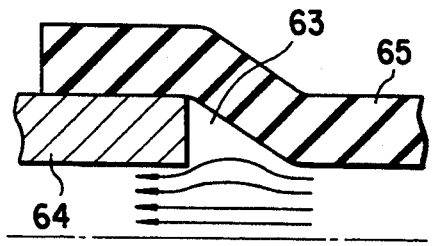
F I G. 27
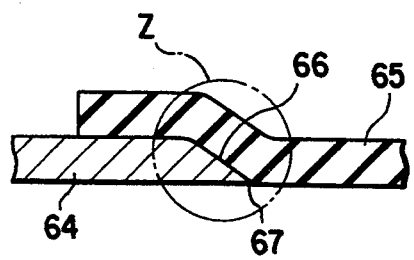
F I G. 28 A
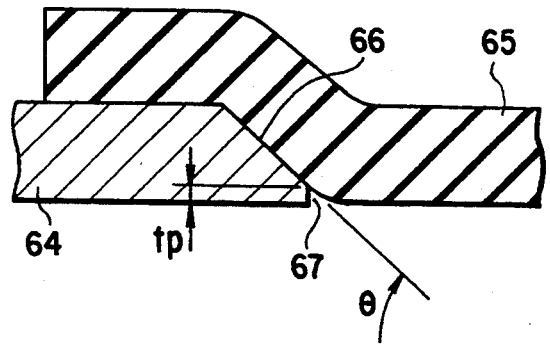
F I G. 28 B
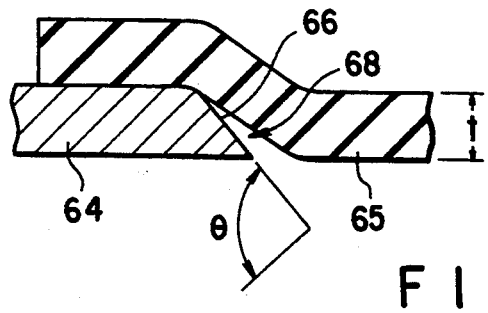
F I G. 29

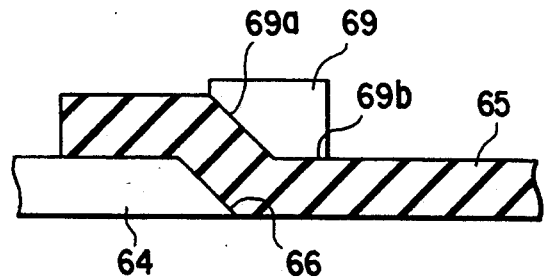
F I G. 30
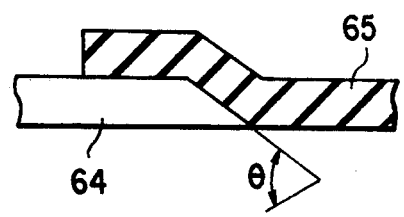
F I G. 31
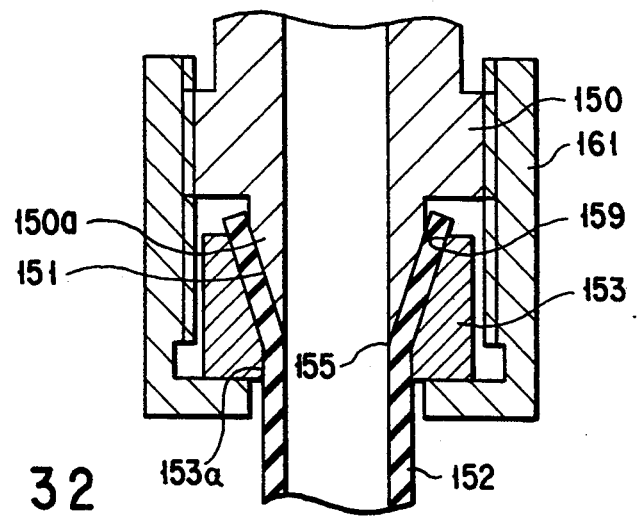
F I G. 32
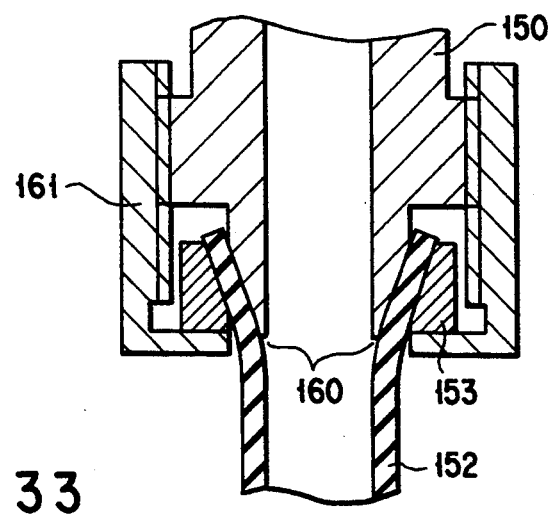
F I G. 33

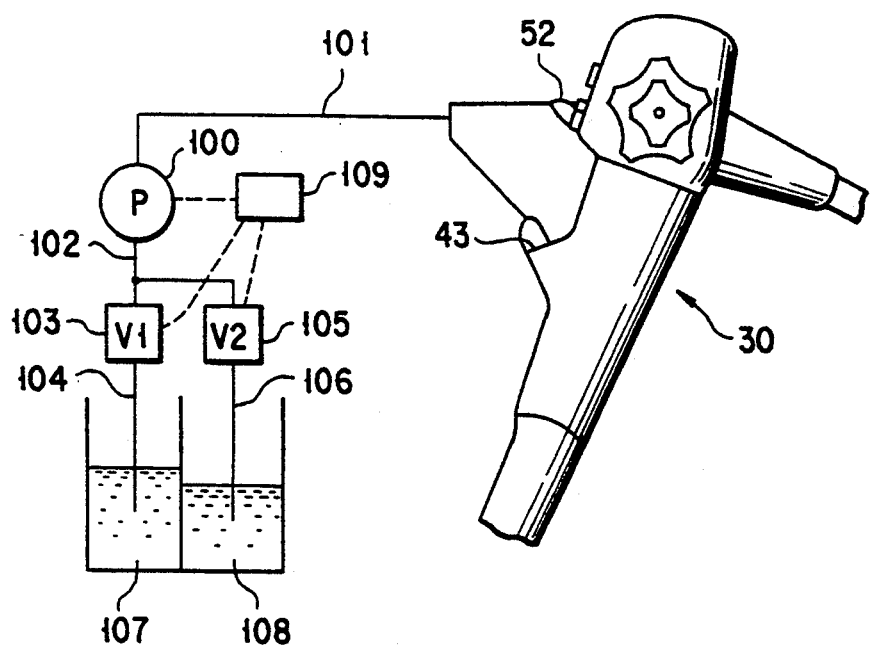
F I G. 39
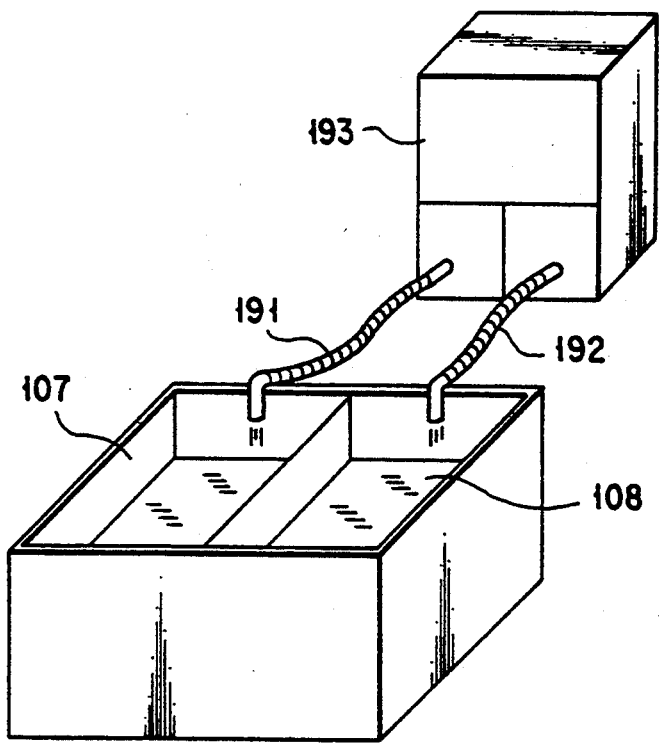
F I G. 40

ENDOSCOPE SYSTEM WHEREIN CLEANING SOLUTION FLOWS AT SAME SPEED IN CLEANING SOLUTION SUPPLY SECTION AND IN ALL FLOW PATHS OF INTERNAL CONDUITS

BACKGROUND OF THE INVENTION

1. Field of the Invention

The present invention relates to an endoscope system for increasing a cleaning power in internal conduits of the endoscope.

2. Description of the Related Art

A cleaning solution such as tap water is generally supplied to clean the internal conduits of an endoscope. To clean paths in the conduits with the cleaning solution flowing through the conduits, the cleaning solution must be hydrodynamically flowed at a flow speed to form a turbulence in the conduit. As a matter of course, the higher the flow speed of the cleaning solution becomes, the better the cleaning effect is, and the shorter the cleaning time becomes. When the flow speed of the cleaning solution is lower than a predetermined speed, the cleaning effect is lost. The flow speed herein is defined as a flow speed V obtained by dividing a flow rate Q per unit time by a sectional area A of the conduit, i.e., V=Q/A.

As described above, the cleaning capability in the internal conduits of an endoscope is regarded to depend on the flow speed of the cleaning solution. The cleaning capability also changes depending on the cleaning power of the cleaning solution itself and the temperature of the cleaning solution. When cleaning is performed using a cleaning solution containing a strong detergent and a high-temperature cleaning solution, contamination caused by an endoscopic examination can be removed. The strong detergent, however, adversely affects the materials of members in the endoscope and may damage the endoscope itself. When the temperature of the cleaning solution is increased, the endoscope itself is damaged. In field applications, tap water is often used to clean endoscopes in a lot of medical facilities. In this case, satisfactory cleaning cannot be achieved by simply supplying a cleaning solution to a conduit.

As described above, to satisfactorily clean the conduits of an endoscope, the cleaning solution must be flowed at a high flow speed and must be hydrodynamically caused to form a turbulence in the conduit.

A turbulence is caused by Reynolds number $Re=2,320$. A relation between the Reynolds number $Re$ and a flow speed $\mu$ of a cleaning solution is represented as follows:

$$Re = \mu \cdot d / \nu$$

where $d$ is the inner diameter of the conduit, $\nu$ is the kinematic viscosity coefficient, and $\mu$ is the flow speed of the cleaning solution, i.e., the value obtained by dividing the flow rate Q per unit time in the conduit by the sectional area A of the conduit, i.e., $\mu = Q/A$ (cm/s).

In a channel (conduit) having an inner diameter of 2.0 mm, for example, a turbulence is formed at 116.4 cm/s according to $\mu = Re \cdot \nu / d$. The kinematic viscosity coefficient $\nu$ is $1.0038 \times 10^{-6}$ m$^2$/s at 20° C. in water. FIG. 1 shows the distribution of velocity vectors v of a cleaning solution b when the cleaning solution b is flowed in a conduit a of an endoscope. As is apparent from FIG. 1, the flow speed is high at the center of the conduit a and decreases near the inner wall surface of the conduit a. It is thus assumed that a turbulence is not formed at the wall surface at $Re \div 2320$.

An experiment was actually conducted to measure a flow speed required for cleaning the inner wall surface of a conduit. In this case, filth containing a protein, which is assumed as a body fluid, was injected in a Teflon channel tube having an inner diameter of 2.0 mm, and tap water was supplied to the tube to clean the interior of the tube. FIG. 2 shows the result in a graph representing a relationship between the cleaning time and the flow speed of the cleaning solution.

As can be apparent from FIG. 2, the cleaning power abruptly increases at a flow speed $\mu = 170$ cm/s or more in the channel having the inner diameter of 2.0 mm. In this case, the Reynolds number is $Re = 3,387$. The conduits of an endoscope must be cleaned at $Re = 3,387$ or more.

The internal conduits in a general endoscope are classified into an air supply conduit, a water supply conduit, a treatment tool insertion conduit, and a suction conduit. To clean the conduits, a cleaning solution is supplied, using a solution supply pump, from the cylinder of a conduit switching valve from which a piston is removed. The maximum inner diameters of the conduits in endoscopes are given as follows. That is, the inner diameter of an insertion-section-side air supply conduit is 1.5 mm, the inner diameter of the water supply conduit is 1.5 mm, the inner diameter of the suction conduit is 5.5 mm, the inner diameter of the universal-cord-side air supply conduit is 2 mm, the inner diameter of the water supply conduit is 2.4 mm, and the inner diameter of the suction conduit is 4 mm.

To clean all these conduits at a flow speed corresponding to $Re = 3,387$ or more, the necessary flow rate Q of the cleaning solution, i.e., $Q = \mu \cdot A = Re \nu/d \times \pi d^2 = Re \cdot \nu \cdot \pi \cdot d / 4$ from $\mu = Q/A'$ and $\mu = Re \nu / d$. For this reason, on the insertion section side, the flow rates Q required to clean the above conduits are 14.69 ml/sec for the suction conduit, 4.01 ml/sec for the air supply conduit, and 4.01 ml/sec for the water supply conduit. On the universal cord side, the flow rates Q required to clean the above conduits are 10.68 ml/sec for the suction conduit, 5.34 ml/sec for the air supply conduit, and 6.41 ml/sec for the water supply conduit. A total flow rate is 45.14 ml/sec = 2708 ml/min. That is, a flow rate of about 3 l/min is required to clean all the internal conduits of the endoscope. When a cleaning solution has this flow rate (about 3 l/min), a flow speed corresponding to $Re = 3,387$ or more can be obtained.

In the prior art, however, a pump for discharging a cleaning solution to these conduits at the above flow rate is not almost taken into consideration. That is, to clean an endoscope having internal conduits, the endoscope is placed in a cleaning tank. A cleaning solution is sprayed from a nozzle arranged in the cleaning tank to the outer surface of the endoscope, and at the same time the cleaning solution is supplied to the internal conduits of the endoscope, thereby cleaning the exterior and interior of the endoscope. In this case, a pump for supplying the cleaning solution to the internal conduits of the endoscope and a pump for supplying the cleaning solution sprayed on the outer surface of the endoscope are normally constituted by a single pump, as is described in Published Unexamined Japanese Utility Model Application No. 64-26005. In this prior art application, although a pump delivery pressure is defined, the flow rate of the cleaning solution is not defined.

In addition to a cleaning scheme for supplying a cleaning solution such as tap water or a detergent in conduits to clean the conduits of the endoscope, a cleaning scheme for supplying a fluid mixture of a cleaning solution and a gas, i.e., a so-called two-phase (gaseous and liquid phases) flow is also known as a scheme for cleaning the conduits in the endoscope. In this two-phase flow cleaning scheme, an exact amount of cleaning solution actually supplied to the conduits of the endoscope to be cleaned cannot be known because the gas supplied from the air supply pump is mixed with the cleaning solution before the cleaning solution is supplied to the conduits.

An endoscope cleaning system having a cleaning pump for cleaning internal conduits can supply a cleaning solution to the conduits of the endoscope. However, the flow rates for the respective conduits are not defined, and a criterion for satisfactorily cleaning the conduit is not clear. A pump having a capability regarded to be appropriate in accordance with the size of a cleaning apparatus and its layout is selected.

Even if a cleaning solution flows at a flow rate for generating a flow speed corresponding to Re=3,387 or more, a recessed portion 202 is present at a joint between conduits 200 and 201 from the microscopic viewpoint, as shown in FIG. 3. The cleaning solution (arrows in FIG. 3 indicate the flow direction of the cleaning solution) tends not to be brought into contact with the inner surface of the conduit at the recessed portion 202. In addition, the cleaning solution stagnates inside the recessed portion 202. It is therefore difficult to obtain a desired flow speed (i.e., a flow speed corresponding to Re=3,387 or more) for satisfactory cleaning.

The internal conduits of the endoscope include a branch point at which one conduit branches into a plurality of conduits and a merging point at which a plurality of conduits merge into one conduit. The branch and merging points are formed by simply connecting conduits having different inner diameters. Flowability of the cleaning solution in the conduits is not taken into consideration upon conduit connection. For example, the inner diameters of the conduits merging at a merging point may be equal to each other, or the inner diameter of an upstream conduit from which a cleaning solution is injected may be much larger than the inner diameter of a downstream conduit.

When the cleaning solution is caused to flow to such a branch point, and conduits merging at this merging point have almost equal inner diameters, the flow speed of the cleaning solution flowing in the downstream conduit decreases by the number of conduits branching on the downstream side. The flow speed in each downstream conduit is much lower than that in the upstream conduit.

When the diameter of an upstream conduit from which a cleaning solution is injected is much larger than that of a downstream conduit, the flow resistance in the downstream conduit is high, and the cleaning solution cannot smoothly flow in the downstream conduit. As a result, the flow speed of the cleaning solution in the upstream conduit also decreases.

In either case, the cleaning powers within the conduits vary, and the conduits cannot be cleaned with a good balance. In other words, even if a cleaning solution is flowed sufficiently, some conduits cannot be satisfactorily cleaned, or the cleaning solution must often be kept flowed to the cleaned conduit so as to clean a conduit in which the flow speed of the cleaning solution is low, thereby wasting the cleaning solution.

When the inner wall surface of a conduit is a rough surface as in a stainless steel pipe, the conduit resistance increases to lower the flow speed of the cleaning solution near the wall surface of the pipe. In the stainless steel pipe, the inner wall surface has a relatively sharp crack-like groove. When such a surface is to be cleaned, it is difficult to bring the cleaning solution into contact with the entire surface, and the cleaning power is low.

In a bent portion of an internal conduit in an endoscope, the flow speed of a cleaning solution flowing on the outer side of the bent portion generally tends to be higher than that flowing on the inner side thereof. Therefore, the cleaning power on the outer side of the bent portion is high, while the cleaning power on the inner side of the bent portion is low.

In consideration of the cleaning powers in the internal conduits of the endoscope, the flow speed and flow rate of the cleaning solution and the conduit structure of the internal conduit are important parameters. In the prior art, almost no consideration has been given to the flow speed and flow rate of the cleaning solution and the conduit structure to clean the internal conduits.

SUMMARY OF THE INVENTION

It is an object of the present invention to provide an endoscope system having a cleaning capacity and a structure, capable of supplying a cleaning solution at a predetermined high flow speed to internal conduits disposed in an endoscope to uniformly and properly clean the interior of each internal conduit of the endoscope.

The object of the present invention is achieved by the following endoscope system. That is, this endoscope system comprises an endoscope having internal conduits, a cleaning solution supply section formed inside the endoscope and communicating with the internal conduits, solution feed means for feeding a cleaning solution to the cleaning solution supply section, and flow regulate means for causing the cleaning solution, supplied from the cleaning solution supply section to the internal conduits by the solution feed means, to flow at a flow speed almost equal to a flow speed in the cleaning solution supply section in all flow paths of the internal conduits.

The solution feed means comprises a solution feed pump for feeding the cleaning solution at a delivery rate of 3.0 (l/min) or more and a delivery pressure of 2.15 (kg/cm$^2$) or more. The flow regulate means comprises means for equalizing a total sectional area on the upstream side with that on the downstream side of the conduit, means for eliminating a step on an inner surface of the conduit, or means for deforming the sectional shape of the conduit.

According to a further aspect of the present invention, an endoscope system comprises an endoscope having at least one conduit means for receiving a cleaning solution; a cleaning solution supply section arranged on said endoscope and connected to said at least one conduit means; and solution feed means, connected to said at least one conduit means through said cleaning solution supply section, for causing a cleaning solution to flow at a first speed approximately identical to a second speed at which the cleaning solution flows through said cleaning solution supply section.

Preferably, the first speed is at least 170 cm/sec.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 11 is a view showing the speed distribution of the cleaning solution flowing through a bent portion of the endoscope conduit;

FIG. 12 is a view showing the distribution of speeds of the cleaning solution flowing through a flat bent portion;

FIG. 13 is a longitudinal sectional view showing a straight portion of the conduit shown in FIG. 12;

FIG. 14 is a longitudinal section view of a bent portion of the conduit shown in FIG. 12;

FIG. 15 is an enlarged sectional view showing a second branch portion formed in an insertion section of the endoscope;

FIG. 17 is an enlarged view of a first branch portion formed in a connector;

FIG. 18 is an enlarged sectional view of a merging portion between an air supply conduit and a water supply conduit;

FIG. 19 is a sectional view showing a structure in which a filler is filled in a recessed portion in FIG. 20 to eliminate the recessed portion;

FIG. 20 is a sectional view showing part of an endoscope conduit having the recessed portion at a joint between a pipe and a tube;

FIG. 21 is a sectional view near a dead end portion of a conduit which is formed by forming a hole in a block member in the endoscope;

FIG. 25 is a timing chart of a solution supply operation of the cleaning apparatus;

FIG. 26 is a timing chart showing a modification of the solution supply operation in FIG. 25;

FIG. 27 is a sectional view showing part of an endoscope conduit having a recessed portion at a joint between a pipe and a tube;

FIG. 28A is a sectional view showing a structure in which a filler is filled in the recessed portion in FIG. 27 to eliminate the recessed portion;

FIG. 28B is an enlarged view of a portion Z in FIG. 28A;

FIG. 29 is a sectional view showing part of an endoscope conduit having a gap at a joint between a pipe and a tube;

FIG. 30 is a sectional view showing a structure in which a tapered joint is formed between a tube and a pipe and a press member is fitted on the tapered joint to eliminate the gap in FIG. 29;

FIG. 31 is a sectional view showing a modification for eliminating the gap in FIG. 29;

FIG. 32 is a sectional view of a properly improved conduit connecting portion;

FIG. 33 is a sectional view showing a conventional conduit connecting portion;

FIG. 39 is a view showing a schematic arrangement of a cleaning apparatus of an endoscope system according to the second embodiment of the present invention; and FIG. 40 is a perspective view showing a water electrolysis unit, a cleaning water tank, and a rinsing water tank of the endoscope system shown in FIG. 39 according to the second embodiment.

DETAILED DESCRIPTION OF THE PREFERRED EMBODIMENTS

Figure 4:
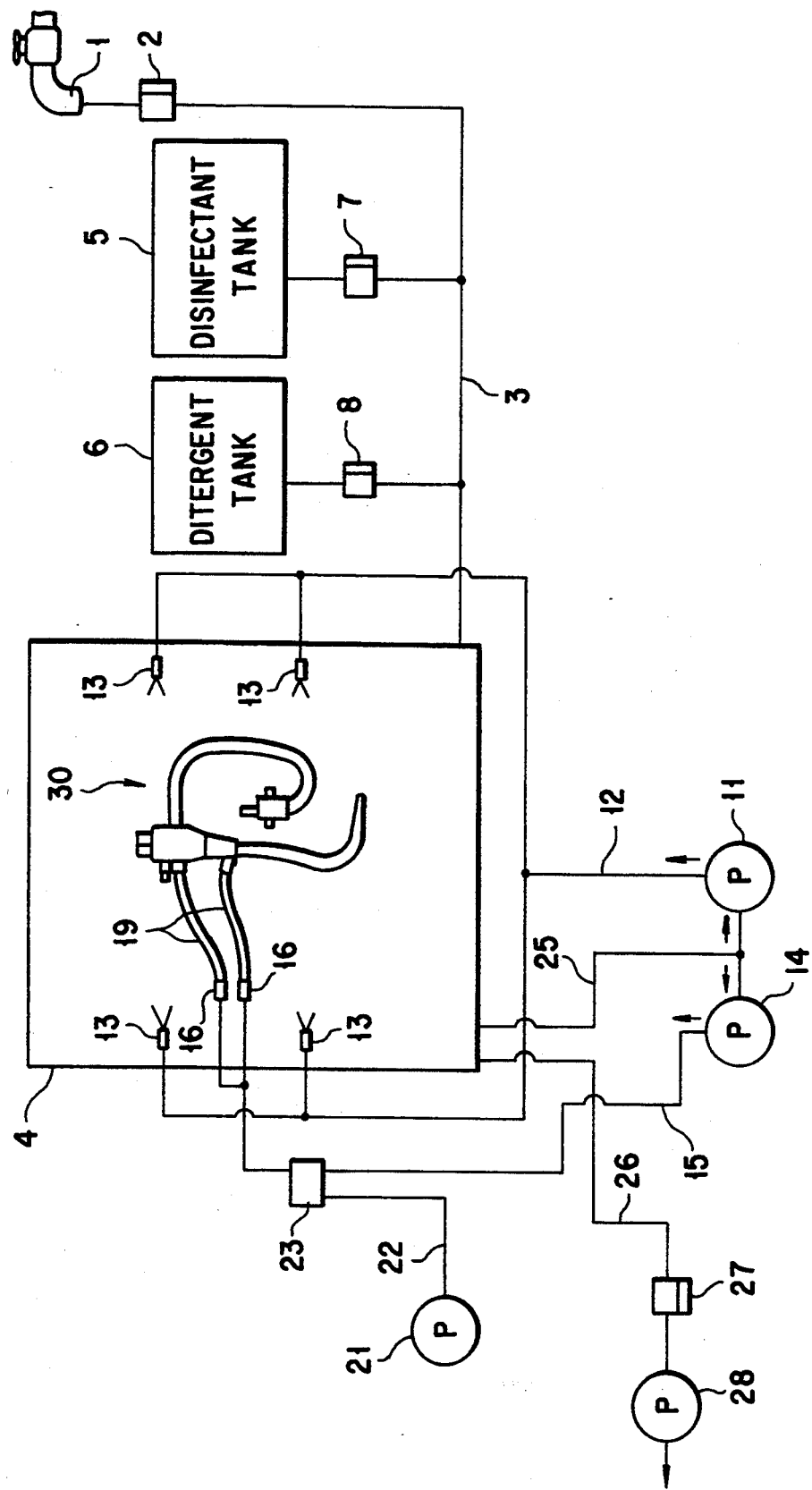
FIG. 4 is a view showing a schematic arrangement of an endoscope system according to the first embodiment of the present invention.

Preferred embodiments of the present invention will be described with reference to the accompanying drawings. FIG. 4 schematically shows the overall arrangement of an endoscope system. Referring to FIG. 4, reference 1 denotes a faucet of tap water. A water supply valve 2 is arranged midway along a water supply path 3, and the water supply path 3 is connected to the faucet 1. The water supply path 3 is connected to the bottom portion of a cleaning tank 4. A disinfectant tank 5 and a detergent tank 6 are connected midway along the water supply path 3 through respective valves 7 and 8 on the upstream side of the water supply valve 2.

The endoscope system has an outer surface cleaning pump 11 and a conduit cleaning pump 14. The outer surface cleaning pump 11 communicates with a plurality of nozzles 13 formed inside the cleaning tank 4 through an outer surface cleaning solution conduit 12. The conduit cleaning pump 14 communicates with a plurality of channel connection ports 16 formed inside the cleaning tank 4 through a conduit cleaning solution supply path 15. Cleaning tubes 19 are detachably connected to the channel connection ports 16, respectively. A cleaning solution or the like is supplied to each internal conduit of an endoscope 30 (to be described later) through the corresponding cleaning tube 19.

A merging portion 23 with an air supply conduit 22 communicating with an air pump 21 is formed midway along the conduit cleaning solution supply path 15. A common conduit 25 communicating with the outer surface cleaning pump 11 and the conduit cleaning pump 14 is connected to the lower portion of the cleaning tank 4. The common conduit 25 serves as a path for returning a cleaning solution or disinfectant collected on the bottom of the cleaning solution 4 to the outer surface cleaning pump 11 and the conduit cleaning pump 14. A water discharge conduit 26 is connected to the bottom wall of the cleaning tank 4. A water discharge valve 27 and a water discharge pump 28 are arranged midway along the water discharge conduit 26. The used cleaning water inside the cleaning tank 4 is externally discharged through the water discharge valve 27 and the water discharge pump 28 along the water discharge conduit 26.

Figure 5:
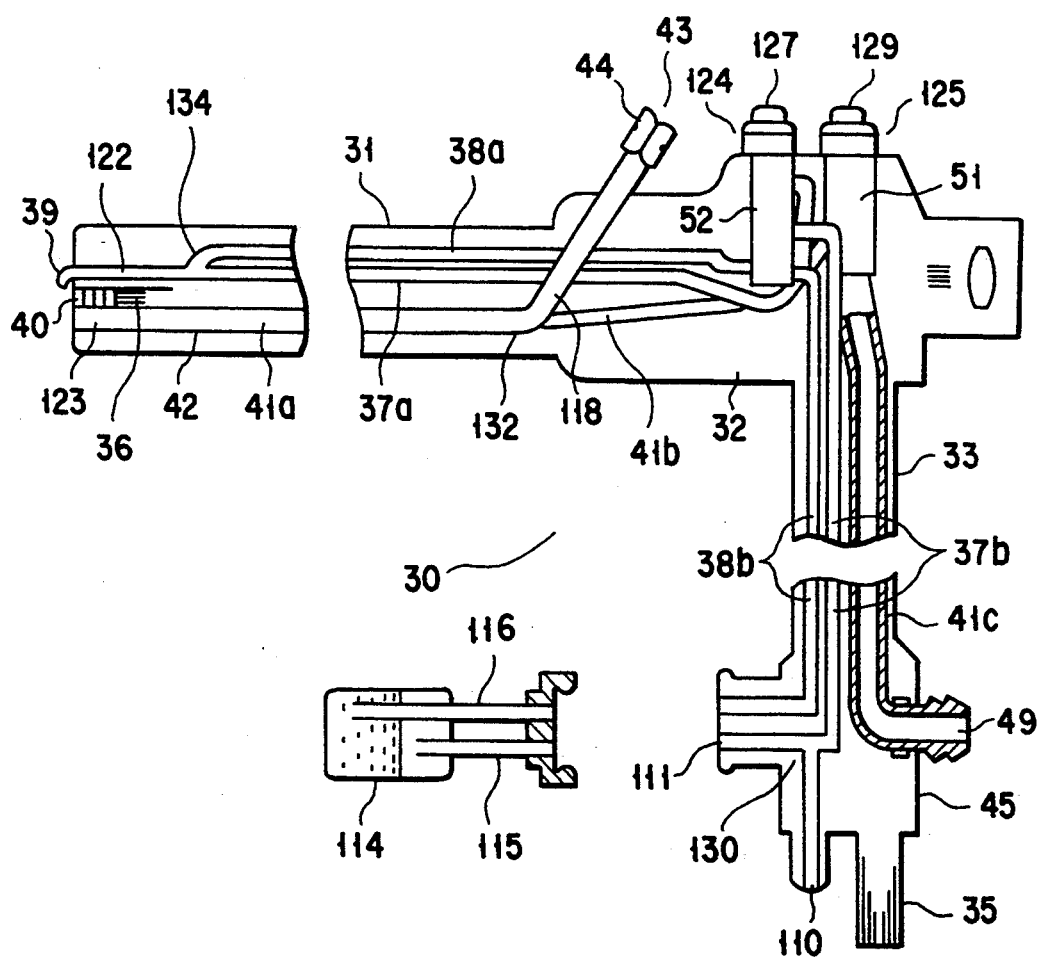
FIG. 5 is a view showing the piping system of an endoscope constituting the endoscope system (one-nozzle type) of the first embodiment of the present invention.

The endoscope 30 to be cleaned is arranged as follows. As shown in FIG. 5, the endoscope 30 has an endoscope body constituted by an insertion section 31 and an operation section 32. The operation section 32 is connected to a universal cord 33 incorporating a light guide fiber bundle 35 therein. The light guide fiber bundle 35 is inserted inside the insertion section 31, the operation section 32, and the universal cord 33, and an image guide fiber bundle 36 extends inside from the insertion section 31 to the operation section 32. Air supply conduits 37 (37a and 37b) and water supply conduits 38 (38a and 38b) are inserted inside and extend through the insertion section 31, the operation section 32, and the universal cord 33 of the endoscope 30.

The first air supply conduit 37a merges with the first water supply conduit 38a inside the distal end portion of the insertion section 31 to constitute a merging portion 134. The conduits 37a and 38a merging at the merging portion 134 extend as a single air/water supply conduit 122 near the distal end portion. The air/water supply conduit 122 is connected to an air/water supply nozzle 39 formed at the distal end of the insertion section 31. The air/water supply nozzle 39 faces the outer surface of an observation window 40 at the distal end of the insertion section 31.

The first air supply conduit 37a and the first water supply conduit 38a are connected to an air/water supply cylinder 52 in an air/water supply switching valve 124 formed in the operation section 32 and communicate with the air/water supply cylinder 52. An air/water supply piston 127 is fitted inside the air/water supply cylinder 52. Air or water is selectively supplied upon depression of the air/water supply piston 127. The second air supply conduit 37b and the second water supply conduit 38b inserted inside the universal cord 33 are also connected to the air/water supply cylinder 52. The second air supply conduit 37b and the second water supply conduit 38b communicate with the air/water supply cylinder 52.

The second air supply conduit 37b branches into a connection conduit 110 and a pressure conduit 111 for compressing a water supply tank 114 to constitute a first branch portion 130 inside a connector 45 connected to the distal end of the universal cord 33. When the connector 45 is connected to a light source unit (not shown), the connection conduit 110 is connected to an air supply pump in the light source unit. The pressure conduit 111 and the second water supply conduit 38b are connected to an air supply tube 115 and a water supply tube 116 on the water supply tank 114 side, respectively. In the connected state, the pressure conduit 111 communicates with the second water supply conduit 38b through the air supply tube 115 and the water supply tube 116.

Suction conduits 41 (41a, 41b, and 41c) extend inside the insertion section 31, the operation section 32, and the universal cord 33. Of these suction conduits 41, the first suction conduit 41a positioned inside the insertion section 31 is formed using a forceps channel 42. The distal end portion of the forceps channel 42 is open to the distal end face of the insertion section 31 to form a suction port 123. A forceps insertion conduit 118 at the proximal end portion of the forceps channel 42 communicating with the first suction conduit 41a is open outside at the operation section 32 to form an insertion port 43. A forceps plug 44 is detachably mounted in the insertion port 43.

The inner portion of the forceps insertion conduit 118 serves as a second branch portion 132 branching into the first suction conduit 41a and the second suction conduit 41b. The second suction conduit 41b is connected to a suction cylinder 51 in a suction control unit 125 arranged adjacent to the air/water switching valve 124 on the side wall of the operation unit 32 and communicates with the interior of the suction cylinder 51. A suction piston 129 is fitted in the suction cylinder 51 to switch between the conduits upon depression of the piston 129 to control suction. The third suction conduit 41c formed in the universal cord 33 is connected to the suction cylinder 51 and communicates with a suction socket 49 formed at the connector 45. The suction socket 49 is connected to a suction tube communicating with a suction bottle and a suction pump (neither are shown).

Figure 1:
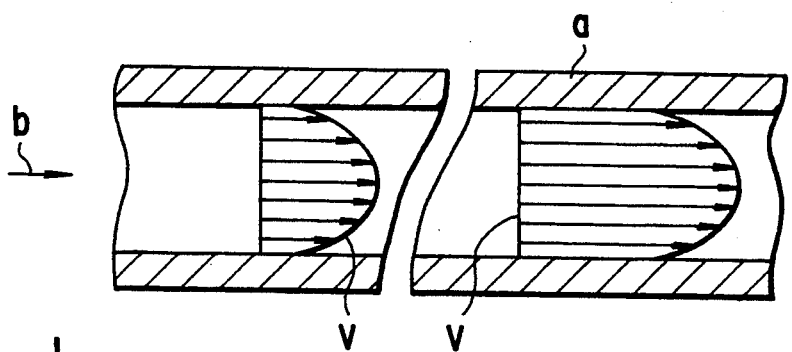
FIG. 1 is a view showing the speed distribution of a cleaning solution flowing in a conduit.
Figure 2:
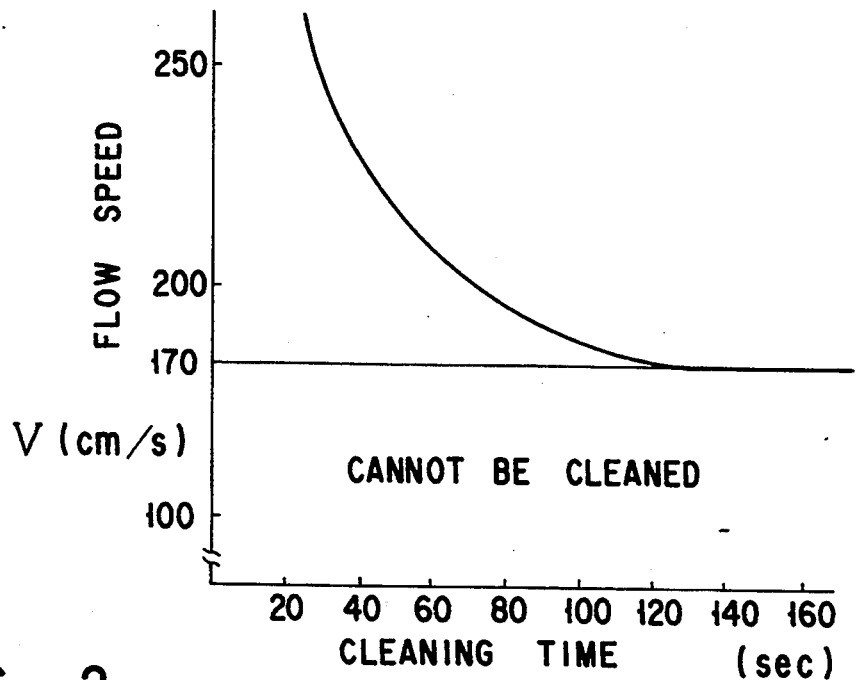
FIG. 2 is a graph showing a relationship between the cleaning time and the speed of the cleaning solution.

As described above, to satisfactorily clean the inner surfaces of the conduits 37, 38, and 41 of the endoscope 30, the cleaning solution must be supplied inside these conduit at a high flow speed. In addition, to clean the inner surfaces of the conduits 37, 38, and 41, a turbulence must be hydrodynamically formed in the flow of the cleaning solution in the conduit. A turbulence is formed at Reynolds number Re=2,320. As can be apparent from the graph in FIG. 2, if a channel has an inner diameter of 2.0 mm, the cleaning power abruptly increases at a flow speed $\mu = 170$ cm/s or more, and the corresponding Reynolds number is Re=3,387. That is, to clean the conduits in the endoscope 30, cleaning must be performed at Re=3,387 or more. If the maximum inner diameters of the first air supply conduit 37a, the first water supply conduit 38a, the first suction conduit 41a (or the second suction conduit 41b), the second air supply conduit 37b, the second water supply conduit 38b, and the third suction conduit 41c are assumed to be 1.5 mm, 1.5 mm, 5.5 mm, 2 mm, 2.4 mm, and 4 mm, respectively, a total flow rate required for causing the cleaning solution to flow in all the conduits 37, 38 and 41 at a flow speed of Re=3,387 or more is 45.14 ml/sec=2,708 ml/min on the basis of the above-mentioned calculation. Therefore, the flow rate of the cleaning solution required to satisfactorily clean the conduits is about 3 l/min.

When a fluid flows along a long conduit, the flow resistance becomes a load. The flow resistance is generally high in a thin conduit. In the endoscope 30, the air supply conduits 37 and the water supply conduits 38 have diameters smaller than that of the suction conduits 41, and the nozzle 39 serving as a resistance is arranged at the distal end of the insertion section 31. For this reason, the flow resistance of the air supply conduits 37 and the water supply conduits 38 is the highest in all the conduits of the endoscope 30. A predetermined pressure or more is required to inject the cleaning solution to the air supply conduits 37 and the water supply conduits 38 at a predetermined flow speed (i.e., a flow speed of Re=3,387 or more).

Figure 6:
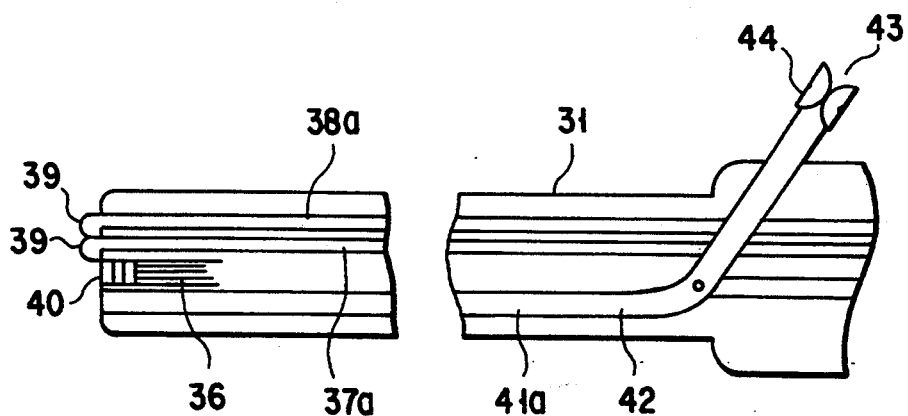
FIG. 6 is a view showing the piping system of an endoscope (two-nozzle type)

The air/water supply piping systems of the endoscopes are classified into a two-nozzle type piping system in which the air supply conduit 37a and the water supply conduit 38a have independent nozzles without any merging portion, as shown in FIG. 6, and a one-nozzle type piping system in which the air supply conduit 37a and the water supply conduit 38a merge into a single conduit, as shown in FIG. 5. The one-nozzle type piping system with a merge structure has a higher conduit resistance than the two-nozzle type piping system. That is, a predetermined flow speed cannot be assured on the upstream side of the merging portion.

Figure 7:
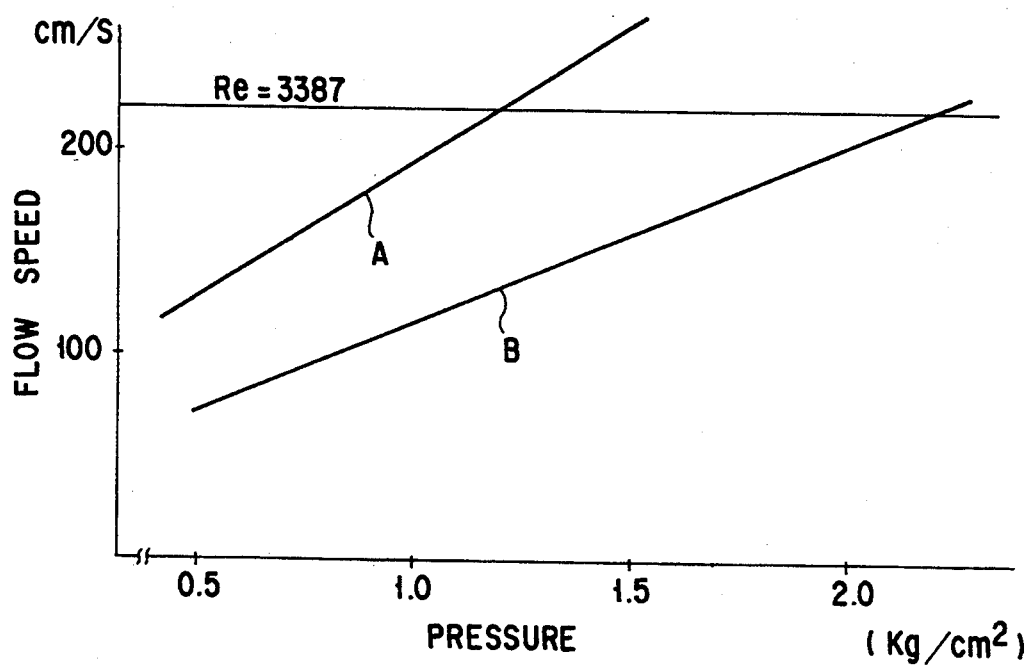
FIG. 7 is a graph showing a relationship between the flow speeds and the pressures in the air/water supply conduits in one- and two-nozzle type endoscopes.

A relationship between the flow speeds and pressures of the air and water supply conduits 37 and 38 is shown in FIG. 7. A characteristic curve A represents the relationship for the two-nozzle type piping system, while a characteristic curve B represents the relationship for the one-nozzle type piping system. It is apparent from the graph that the two- and one-nozzle type piping systems require pressures of 1.2 kg/cm$^2$ or more and 2.15 kg/cm$^2$ or more, respectively, to clean the air and water supply conduits at a flow speed corresponding to Re=3,387 or more. The cleaning pump for cleaning the air and water supply conduits must have a delivery pressure of 1.2 kg/cm$^2$ or more for the two-nozzle piping system and a delivery pressure of 2.15 kg/cm$^2$ or more for the one-nozzle piping system.

The conduit cleaning pump 14 in this embodiment has a delivery rate of 3.5 (l/min) or more and a delivery pressure of 2.15 (kg/cm$^2$).

Figure 8:
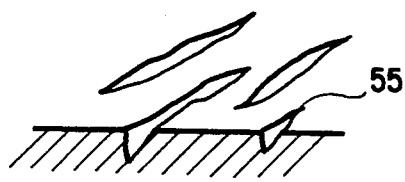
FIG. 8 is a sectional view showing part of an endoscope conduit having cracks in its inner surface.
Figure 9:
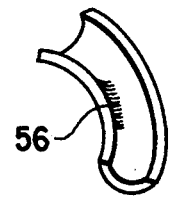
FIG. 9 is a view showing the interior of a bent portion of an endoscope conduit having wrinkles on its inner surface.
Figure 10:
FIG. 10 is a view showing a state in which the inner surface of an endoscope conduit is chemically polished.

The details of the piping of this endoscope 30 will now be described in detail. In the conduits of the endoscope 30, a portion for connecting, e.g., a tube and a socket or cylinder, and a bent conduit around the suction socket 49 are made of stainless steel conduits. The inner surface of such a conduit has relatively sharp crack-like grooves 55, as shown in FIG. 8. In such a pipe, it is difficult to bring the cleaning solution into contact with the entire surface, and the cleaning power is low. Wrinkles 56 caused by plastic deformation are formed on the inner bent surface in the bent portion of a conduit, as shown in FIG. 9. The cleaning power in this portion is also low. In the endoscope 30, the inner surface of the stainless steel conduit is chemically polished. The inner surface of this metal conduit is constituted by a flat surface having a smooth three-dimensional pattern 57, as shown in FIG. 10, thereby increasing the cleaning power.

The above treatment is not limited to chemical polishing, but can be electrolytic polishing, mechanical polishing, coating, or the like. The pipe to be bent is bent, and its inner surface is smoothed to smoothly form the wrinkles 56, thereby considerably increasing the cleaning power. When a conduit does not comprise a stainless steel conduit, but a conduit or tube made of a super-elastic material, formation of wrinkles and the like can be minimized.

In the conduits of the endoscope 30, and particularly, in a bent portion near the suction socket 49 or bent portions around the cylinders 51 and 52, the flow speed of the cleaning solution flowing on the outer side of a bent portion is higher than that flowing on the inner side thereof, as shown in FIG. 11. Reference numeral 59 denotes vectors representing the flow speed of the cleaning solution at a bent portion 60. A high cleaning power can be obtained on the outer side of the bent portion 60, but it is difficult to obtain a high cleaning power on the inner side of the bent portion 60. To reduce the difference between the cleaning powers on the outer and inner sides, the bent portion 60 of the conduit is flattened, as shown in FIG. 12 (the cross-section is shown in FIG. 14). A minor axis D2 of the bent portion 60 in FIG. 12 is smaller than an inner diameter D1 of a circular portion 61 (the cross-section is shown in FIG. 13). That is, D1>D2. According to this relation, the difference between the flow speeds on the outer and inner sides of the bent portion 60 is reduced, and almost equal cleaning powers are obtained on the outer and inner sides. In this case, however, when the minor axis of the flat bent portion is excessively reduced, a cleaning brush cannot be inserted into this flat bent portion. In a normal case, the flattening degree, i.e., the ratio D2/D1 is preferably set to be 70% or more. The center of the conduit of the flat bent portion may be displaced to the inner or outer side.

The sectional area of the merging portion between the second suction conduit 41b and the first suction conduit 41a (forceps channel 42) in the conventional endoscope is set to be considerably large. When this sectional area is large, the flow speed of the cleaning solution in this area is reduced, and a prescribed cleaning power cannot be assured. In this embodiment, as shown in FIG. 15, a sectional area S of the second branch portion 132 is set to be smaller than the sectional area of a largest-diameter conduit portion in the endoscope 30. The largest-diameter conduit portion is the insertion port 43 (forceps insertion conduit 118) in the suction piping in the endoscope 30. To clean the suction piping system, a cleaning solution is injected from this insertion port 43.

In the structure of this embodiment, as shown in FIG. 15, a sectional area S of the conduit at the second branch portion 132 is smaller than a sectional area N of the conduit at the insertion port 43 (forceps insertion conduit 118) to assure the prescribed flow speed of the cleaning solution at the insertion port 43. The pump capacity is set, so that the predetermined or prescribed flow speed can be assured even at the largest-diameter conduit portion in the conduits of the endoscope 30 during cleaning. Therefore, the cleaning solution flows at the predetermined speed or more even at the second branch portion 132, thereby assuring a high cleaning power.

At the second branch portion 132, the second suction conduit 41b is formed at a straight portion in the forceps insertion conduit 118. For this reason, when forceps and the like are to be removed through the insertion port 43, they will not be caught by the second branch portion 132.

Figure 16:
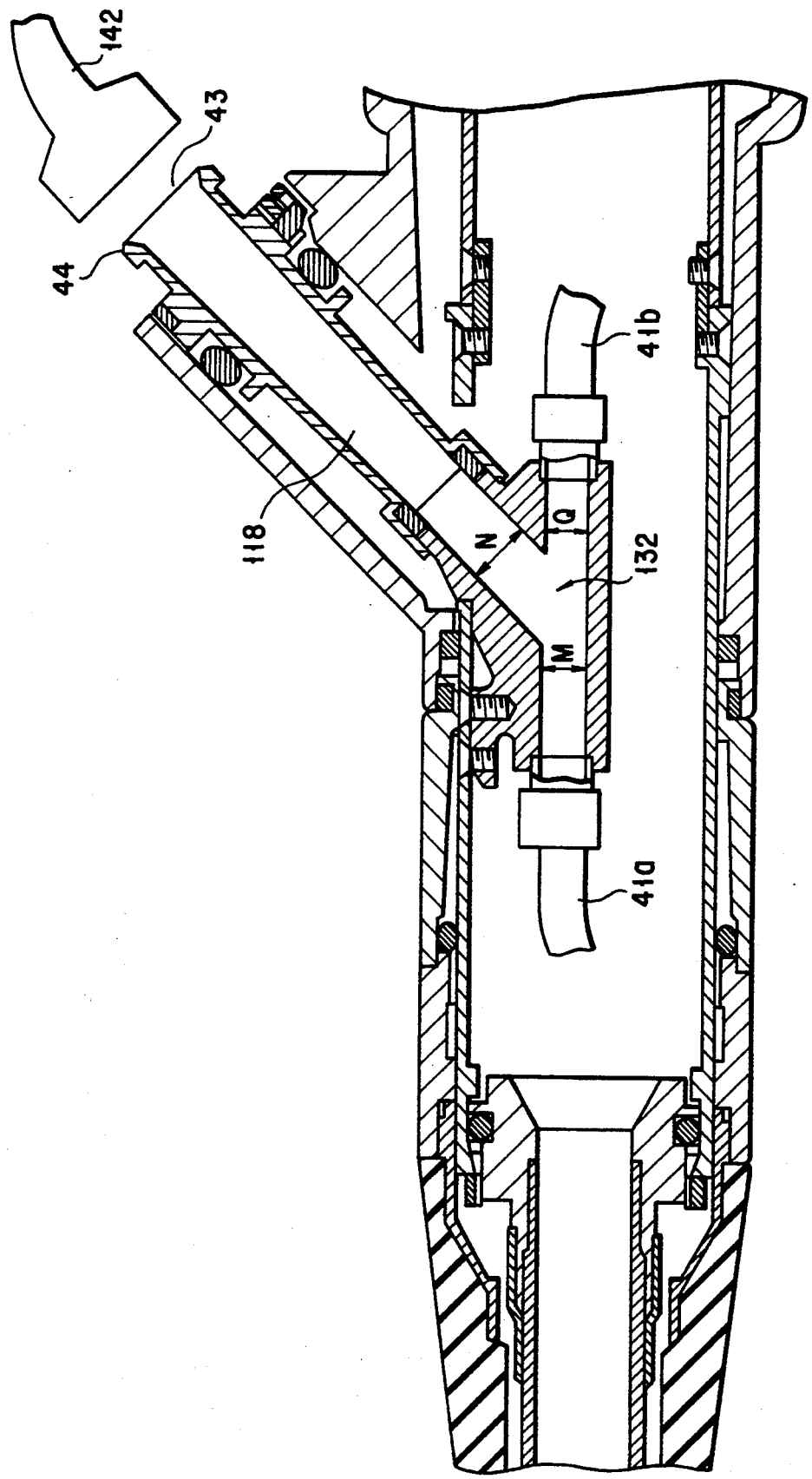
FIG. 16 is a sectional view showing a modification of the structure shown in FIG. 15.

FIG. 16 shows a modification of the structure of the second branch portion 132. In the second branch portion 132, an inner diameter M of the first suction conduit 41a (forceps channel 42), an inner diameter Q of the second suction conduit 41b, and an inner diameter N of the forceps insertion conduit 118 satisfy relation $N^2 = M^2 + Q^2$. More specifically, in the three conduits, i.e., the first suction conduit 41a, the second suction conduit 41b, and the forceps insertion conduit 118, which merge at the second merging portion 132, the sectional area of the forceps insertion conduit 118 located on the upstream side of the second branch conduit 132 from which the cleaning solution is supplied is set to be equal to the sum of the sectional areas of the first and second suction conduits 41a and 41b located at the downstream side and merging at the second branch portion 132. The cleaning solution injected from the insertion port 43 flows at an almost constant speed in the forceps insertion conduit 118, the first suction conduit 41a, and the second suction conduit 41b. Injection of the cleaning solution from the forceps insertion conduit 118 can sufficiently assure the flow speed and flow rate of the cleaning solution as compared with the conventional case in which the cleaning solution is injected from the suction cylinder 51.

The inner diameters of the conduits constituting the first branch portion 130 located in the connector 45 will be described below with reference to FIG. 17. As previously described, the first branch portion 130 is formed by branching the second air supply conduit 37b into the connection conduit 110 and the pressure conduit 111. In this case, an inner diameter I of the second air supply conduit 37b, an inner diameter A of the connection conduit 110, and an inner diameter B of the pressure conduit 111 satisfy relation $I^2 = A^2 + B^2$. That is, in the three conduits, i.e., the connection conduit 110, the pressure conduit 111, and the second air supply conduit 37b, which merge at the first branch portion 130, the sectional area of the second air supply conduit 37b located on the upstream side of the first branch portion 130 in which the cleaning solution flows is set to be equal to the sum of the sectional areas of the connection and pressure conduits 110 and 111 located on the downstream and merging at the first branch portion 130. The cleaning solution flowing from the second air supply conduit 37b (upstream side) flows at an almost constant speed in the connection conduit 110 and the pressure conduit 111. Therefore, these three conduits 37b, 110, and 111 can be uniformly cleaned.

The inner diameters of the conduits forming the merging portion 134 located in the insertion section 31 will be described with reference to FIG. 18. In this merging portion 134, an inner diameter J of the first water supply conduit 38a, an inner diameter H of the first air supply conduit 37a, and an inner diameter C of the air/water supply conduit 122 have relation $C^2 = J^2 + H^2$. In the three conduits, i.e., the first water supply conduit 38a, the first air supply conduit 37a, and the air/water supply conduit 122 which merge at the merging portion 134, the sum of the sectional areas of the first water supply conduit 38a and the first air supply conduit 37a which are located on the upstream of the merging portion 134 in which the cleaning solution flows is set to be almost equal to the sectional area of the air/water supply conduit 122 located on the downstream side and merging at the merging portion 134. The cleaning solution flows in the air/water supply conduit 122 at almost the same speed as that of the cleaning solution flowing in each of the first air supply conduit 37a and the first water supply conduit 38a.

FIGS. 19 and 20 show structures of the distal end constituting portions of the distal end of the insertion section 31. Reference numeral 75 in FIG. 19 denotes a distal end constituent portion body. For example, a pipe 77 connected to a tube 76 constituting the treatment tool insertion channel 42 is connected to the distal end constituent portion body 75. A distal end cover 78 made of a resin is mounted on the distal end constituent portion body 75 to insulate the endoscope from a body wall. In this structure, a recessed portion 79 shown in FIG. 20 is formed at a joint between the distal end constituent portion body 75 and the pipe 77 or the distal end cover 78. A filler 80 containing, e.g., a silver-based antibacterial agent is filled in the recessed portion 79 to eliminate the recessed portion 79 (FIG. 19). As this filler 80, an epoxy-based adhesive or a silicone-based filler is used. The recessed portion 79 is filled with the filler 80 to obtain a smooth surface even at a joint between conduits, thereby performing satisfactory cleaning while assuring the predetermined flow speed at the respective portions of the conduit joints.

When conduits 121 and 122 are to be formed by forming holes in a block member 120 such as the connector 45 and the distal end constituent portion of the endoscope 30, recessed dead end portions 81 are formed, as shown in FIG. 21. In this case, when the dead end portions 81 are left untreated, the cleaning solution does not flow into the dead end portions 81, thereby lowering the cleaning power at these portions. In the endoscope 30, the filler 80 is injected into these dead end portions 81 to eliminate the recessed portions. The filler 80 is injected as follows. The filler is injected from the bottom of the dead end portion 81 using a dispenser such as a syringe. When the filler 80 is sufficiently filled in the dead end portion 81, a fluid such as air or a cleaning solution is supplied to this conduit to discharge an extra filler, thereby closing the dead end portions 81. Therefore, even if a structure in which a dead end portion 81 is inevitably formed is employed, a piping system which can be satisfactorily cleaned can be provided.

In injecting the cleaning solution to the air supply conduits 37 and the water supply conduits 38 in the endoscope, the cleaning solution is fed from the air/water supply cylinder 52. In injecting the cleaning solution in the suction conduits 41, as described above, the cleaning solution is fed from the treatment tool insertion port 43. The cleaning tubes 19 and a cleaning tube 142 are connected to the cylinder 52 and the insertion port 43.

Figure 22:
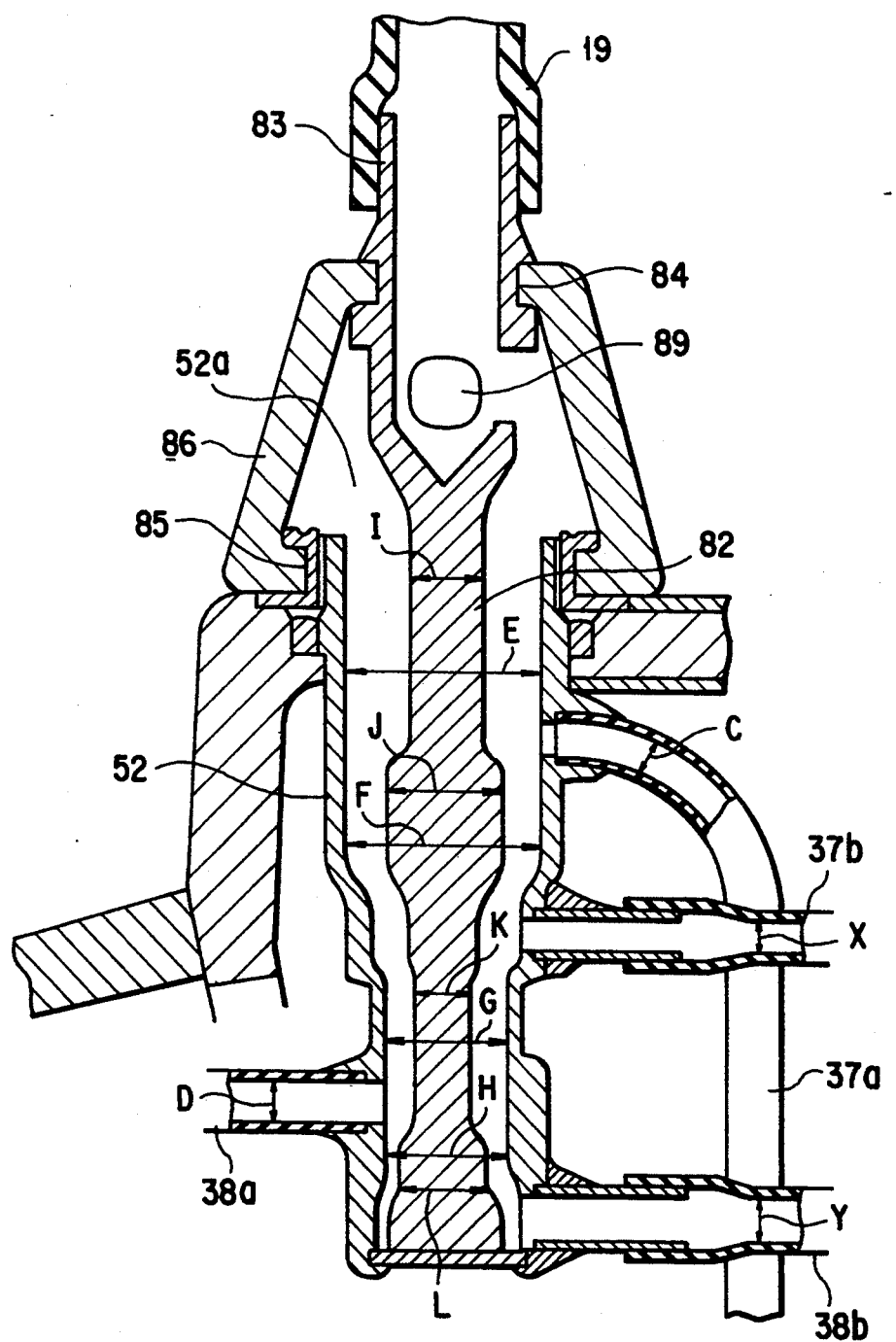
FIG. 22 is a sectional view showing a piping arrangement near an air/water supply cylinder of the endoscope.

As shown in FIG. 22, a total of four conduits, i.e., the air and water supply conduits 37b and 38b on the universal cord 33 side, and the air and water supply conduits 37a and 38a on the insertion section 31 side, are open to the inner wall surface of the air/water supply cylinder 52. The inner diameter of the cylinder 52 between these conduits (37a, 37b, 38a, and 38b) is gradually reduced stepwise. An air/water supply piston (not shown) is inserted into this air/water supply cylinder 52. This piston has a diameter much larger than the inner diameter of each conduit so as to control air/water supply. The inner diameter of the air/water supply cylinder 52 from which the piston is removed is much larger than the inner diameter of each conduit. For this reason, even if the cleaning solution flows in each conduit at the predetermined flow speed, the cleaning solution cannot flow in the inner wall of the cylinder at this predetermined flow speed. That is, the flow speed is reduced.

In this embodiment, as shown in FIG. 22, the cleaning tube 19 is connected to the air/water supply cylinder 52 while a core 82 is kept inserted and disposed in the cylinder 52 to increase the flow speed of the cleaning solution. The proximal portion of the core 82 comprises a portion 83 fitted on the cleaning tube 19 and a portion 84 mounted with a mounting member 86 connected to a mounting seat 85 formed at an opening 52a of the air/water supply cylinder 52. An injection port 89 for guiding the cleaning solution from the cleaning tube 19 to the cylinder 52 is formed in the core 82.

The outer diameter of the core 82 is set such that the cleaning solution flows on the inner wall of the air/water supply cylinder 52 at the predetermined flow speed, while the core 82 is kept inserted in the air/water supply cylinder 52. More specifically, assume that the inner diameters of the air and water supply conduits 37b and 38b on the universal cord 33 side and the air and water supply conduits 37a and 38a on the insertion section 31 side are defined as X, Y, C, and D, respectively. Also assume that the inner diameter between the opening 52a and the air supply conduit 37a in the inner diameter of the air/water supply cylinder 52, the inner diameter between the air supply conduits 37a and 37b therein, the inner diameter between the air supply conduit 37b and the water supply conduit 38a therein, and the inner diameter between the water supply conduits 38a and 38b therein are defined as E, F, G, and H, respectively. The outer diameter between the conduits of the core 82 are also similarly defined as I, J, K, and L, respectively. In this case, the outer diameter of the core 82 is determined to satisfy the following equations:

$$I^2 = E^2 - (X^2 + Y^2 + C^2 + D^2)$$

$$J^2 = F^2 - (X^2 + Y^2 + D^2)$$

$$K^2 = G^2 - (Y^2 + D^2)$$

$$L^2 = (H^2 - Y^2)$$

The clearance area between the air/water supply cylinder 52 and the core 82 along the flow of the cleaning solution is set to be equal to the sum of the sectional areas of the conduits connected to the downstream side of the core 82. The core 82 is arranged such that the cleaning solution can flow on the inner wall of the air/water supply cylinder 52 at the same flow speed as that in each conduit. This structure is not limited to cleaning of the air/water supply cylinder 52, but can be applied to a large-diameter conduit which makes it difficult to obtain a predetermined flow speed. That is, a core member is inserted in such a thick conduit which makes it difficult to obtain the predetermined flow speed. Therefore, the flow speed is increased to improve the cleaning effect.

Figure 23:
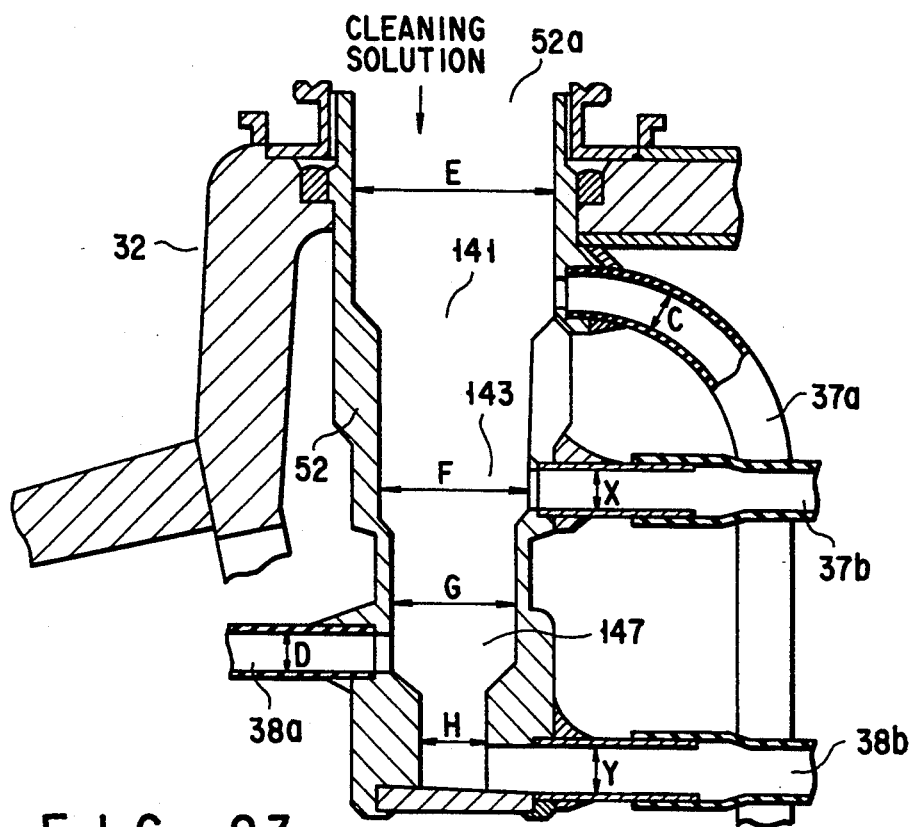
FIG. 23 is a sectional view showing a modification of the structure shown in FIG. 22.

FIG. 23 shows another structure in which the cleaning solution can flow along the inner wall of the air/water supply cylinder 52 and in each conduit at the same flow speed. In this structure, the air/water supply cylinder 52 is formed, so that the inner diameters E, F, and C satisfy condition $E^2 = F^2 + C^2$.

That is, in the three conduits (the portion of the cylinder 52 which has the inner diameter E, the first air supply conduit 37a, and the portion of the cylinder 52 which has the inner diameter F) merging at a branch point 141, the sectional area of the portion of the cylinder 52 which has the inner diameter E and is located on the upstream side of the branch point 141 in which the cleaning solution flows is set to be almost equal to the sum of the sectional areas of the first air supply conduit 37a and the cylinder 52 portion having the inner diameter F which are located on the downstream side and merge at the branch point 141.

The inner diameters F, G, and X satisfy relation $F^2 = G^2 + X^2$. More specifically, in the three conduits (i.e., the portion of the cylinder 52 which has the inner diameter F, the second air supply conduit 37b, and the portion of the cylinder 52 which has the inner diameter G) merging at a branch point 143, the sectional area of the portion of the cylinder 52 which has the inner diameter F and is located on the upstream side of the branch point 143 in which the cleaning solution flows is set to be almost equal to the sum of the sectional areas of the second air supply conduit 37b and the cylinder 52 portion having the inner diameter G which are located on the downstream side and merge at the branch portion 143.

The inner diameters G, H, and D satisfy relation $G^2 = H^2 + D^2$. More specifically, in the three conduits (the portion of the cylinder 52 which has the inner diameter G, the first water supply conduit 38a, and the portion of the cylinder 52 which has the inner diameter H) merging at a branch point 147, the sectional area of the portion of the cylinder 52 which has the inner diameter G and is located on the upstream side of the branch point 147 in which the cleaning solution flows is set to be almost equal to the sum of the sectional areas of the first water supply conduit 38a and the cylinder 52 portion having the inner diameter H which are located on the downstream and merge at this branch point 147. An inner diameter Y of the second water supply conduit 38b is set to be almost equal to the inner diameter H of the cylinder 52 portion extending from the first water supply conduit 38a to the second water supply conduit 38b due to the same reason as described above.

The inner diameters (E, F, G, H, C, X, D, and Y) are thus defined. The cleaning solution injected from the cylinder opening 52a flows in the conduits (the respective inner-diameter portions of the cylinder 52, the air supply conduits 37a and 37b, and the water supply conduits 38a and 38b) through the branch points 141, 143, and 147 of the air/water supply cylinder 52 at an almost constant flow speed, thereby uniformly cleaning the respective conduits.

Figure 24:
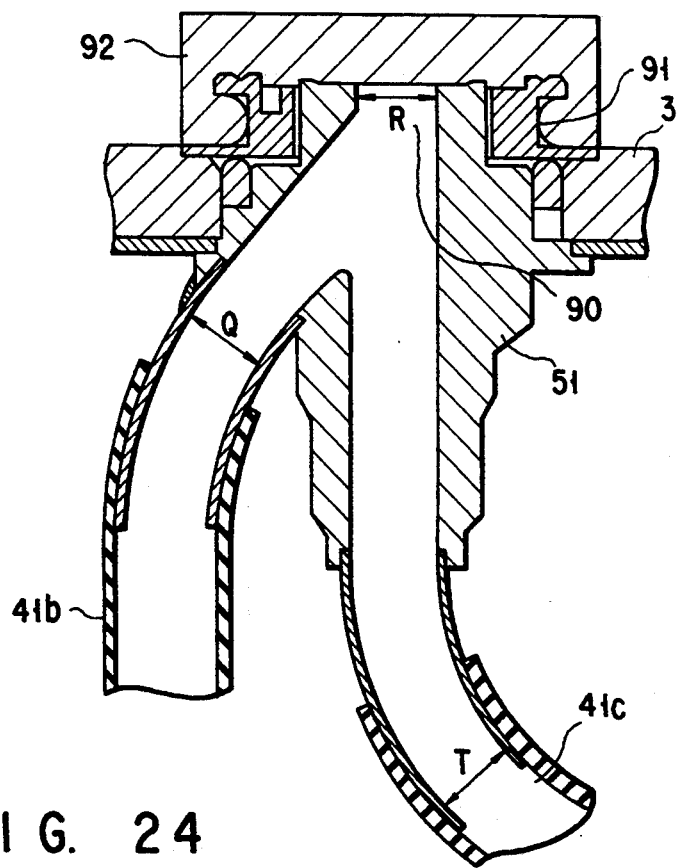
FIG. 24 is a sectional view of a suction cylinder.

The suction conduits 41 are cleaned as follows. As shown in FIG. 24, while a lid 92 is placed on a mounting seat 91 formed in an opening 90 of the suction cylinder 51, the cleaning solution is injected from the forceps insertion conduit 118 to the suction conduits 41 through the second branch portion 132. In this case, as shown in FIG. 16, the cleaning tube 142 connected to a cleaning machine (not shown) is connected to the insertion port 43 of the forceps insertion conduit 118.

In the suction cylinder 51 in which the second suction conduit 41b is connected to the third suction conduit 41c, an inner diameter Q of the second suction conduit 41b, an inner diameter T of the third suction conduit 41c, and an inner diameter R of the suction cylinder 51 satisfy relation $Q^2 = R^2 = T^2$. Therefore, the cleaning solution can flow through all the suction conduits 41a, 41b, and 41c at the same flow speed.

Assume that the cleaning solution is injected from the suction cylinder 51 to clean the suction conduits 41 as in the conventional case. To flow the cleaning solution in the suction conduits 41a, 41b, and 41c at the same flow speed, the inner diameters of these suction conduits must satisfy relation $R^2 = T^2 + Q^2 = T^2 + M^2 + N^2$. In this case, the diameter of the second suction conduit 41b must be largely increased to disadvantageously result in a bulky operation section 32. However, according to this embodiment, when the cleaning solution is injected from the insertion port 43, the operation section 32 can be advantageously made compact.

Figure 3:
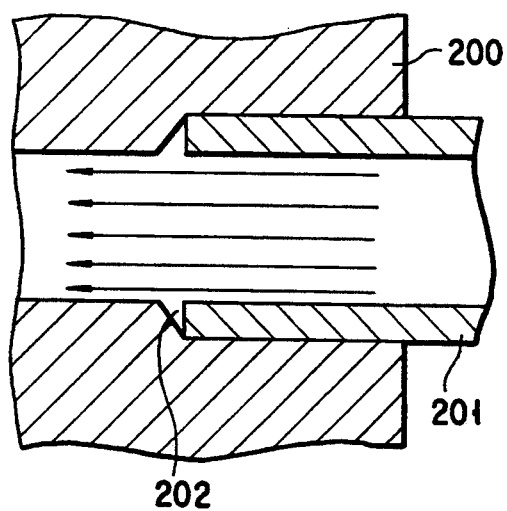
FIG. 3 is a sectional view of a conventional conduit connecting portion.

The conduits 37, 38, and 41 in the endoscope 30 are formed as described above to cause the cleaning solution to flow in the conduits 37, 38, and 41 at the same flow speed. From the microscopic viewpoint, a recessed portion 202 is present at the joint between conduits 200 and 201, as shown in FIG. 3. The cleaning solution (arrows indicate the flow of the cleaning solution) tends not to be brought into sufficient contact with the recessed portion 202, and it is difficult to obtain a desired flow speed enough to satisfactorily clean the recessed portion 202. A countermeasure against such a local portion will be described below.

A recessed portion 63 is formed at a joint between conduits such as between a tube and a pipe, as shown in FIG. 27. Reference numeral 64 denotes a pipe; and 65, a tube connected to the pipe 64. The relatively large recessed portion 63 is formed at the boundary between the end face of the pipe 64 and the inner surface of the tube 65, and the cleaning solution stagnates in the recessed portion 63, and the predetermined flow speed cannot be assured. In this embodiment, the joint between the conduits is constituted as follows. The end face of the pipe 64 is constituted by a tapered portion 66, and the tapered portion 66 is brought into tight contact with the inner surface of the tube 65 at the joint (FIGS. 28A and 28B), thus eliminating the recessed portion 63 formed between the tube 65 and the pipe 64.

A Teflon tube such as PTFE tube is generally used as the tube 65 in the piping of the endoscope 30 in consideration of a cleaning power and resistance to chemicals. A tube of this type is relatively rigid and cannot be bent at an acute angle. The taper angle $\theta$ (FIG. 28A) of the tapered portion 66 at the end face of the pipe 64 is set to be 90° or less, and a thickness tp of an end face 67 is set to be 1 mm or less, thereby suppressing formation of the recessed portion 63 at the joint. The same cleaning power as in the inner surface of an almost straight tube portion can be obtained.

When a thickness t of the tube 65 is particularly large, a gap 68 may be formed between the tube 65 and the pipe 64 even if the taper angle $\theta$ is set to be 90° or less, as shown in FIG. 29. In this case, as shown in FIG. 30, a press member 69 can be disposed to forcibly bond the tube 65 and the pipe 64. More specifically, the press member 69 has a tapered portion 69a having almost the same angle as the taper angle of the tapered portion 66 formed in the pipe 64 and a parallel portion 69b for pressing the tube 65 to set the inner diameter of the pipe 64 to be equal to the inner diameter of the tube 65. Thus, the gap 68 between the tube 65 and the pipe 64 is eliminated to increase the cleaning power. The tapered portion 66 of the pipe 64 will not peel from the tube 65 even if a bending force as in bending acts on the connecting portion between the tube 65 and pipe 64.

If the tube 65 has a thickness enough to be used in the endoscope 30, and the taper angle $\theta$ of the pipe 64 is set to be 60° or less, as shown in FIG. 31, elimination of the gap between the pipe 64 and the tube 65 is experimentally confirmed.

When the joint between the pipe 64 and the tube 65 having the above structure, however, is placed in the bending portion of the insertion section 31, and the bending portion is bent, a gap between the pipe 64 and the tube 65 tends to be formed. If filth enters through the gap during examination upon bending, the gap is eliminated from the bending portion returned to a straight state during cleaning, and the filth between the pipe and the tube cannot be cleaned. Even if a bending force directly acts on the pipe 64 and the tube 65, the pipe 64 must be prevented from peeling from the tube 65. When the joint between the pipe 64 and the tube 65 is formed in a hard portion of the distal end portion of the insertion section 31, the tapered end face 66 of the pipe 64 will not peel from the tube 65.

Reference numeral 152 in FIG. 32 denotes a tube constituting a conduit. The distal end portion of the tube 152 is inserted under pressure into a tube connecting portion 150a at the distal end of a socket 150 while spreading along a tapered surface 151 of the connecting portion 150a. The tube 152 is pressed by a tapered surface 159 of a press member 153 which has a taper angle almost equal to or slightly larger than the tapered surface 151. In this case, the press member 153 is kept pressed by a nut 161 threadably engaged with the socket 150. In this state, the pressure member 153 clamps the distal end portion of the tube 152 between its tapered surface 159 and the tapered surface 151 of the connecting portion 150a, thereby assuring water-tightness of a conduit formed by the inner hole of the socket 150 and the inner hole of the tube 152.

In the above structure, the tapered surface 151 of the tube connecting portion 150a at the distal end of the socket 150 extends up to the position of a distal end 155 of the tube connecting portion 150a. The tapered surface 159 of the press member 153 extends up to almost the position of the distal end 155 of the tube connecting portion 150a and properly presses the tube 152 up to the distal end 155 of the tube connecting portion 150a. The press member 153 has a tubular portion 153a having almost the same inner diameter as that of the socket 150 or the tube 152 to prevent spreading of the tube 152. Therefore, a recessed portion 160 shown in FIG. 33 is not formed in the connecting portion between the tube 152 and the socket 150, thereby perfectly cleaning the paths in the conduits.

Figure 34:
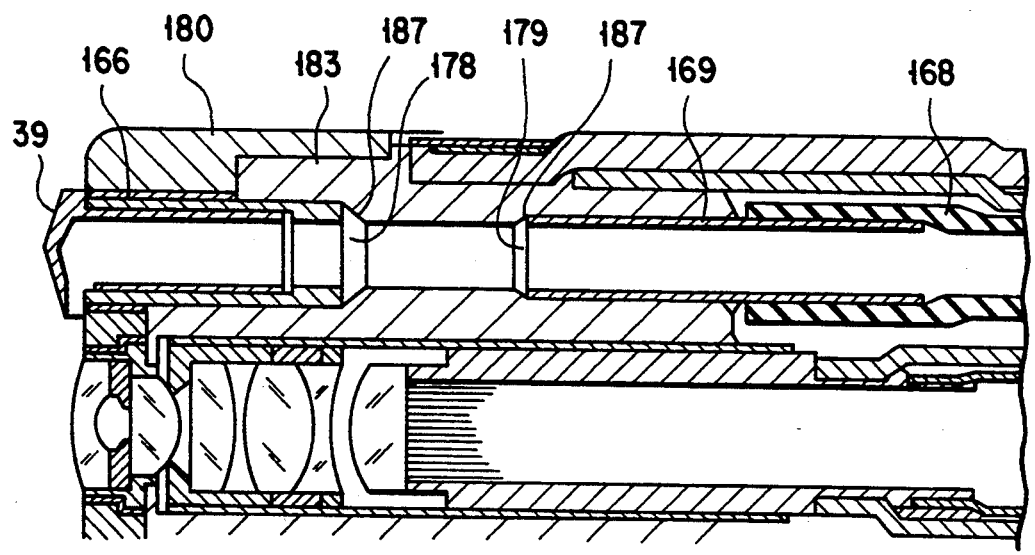
FIG. 34 is a sectional view showing a conventional conduit connecting portion at a distal end portion of an endoscope.

The above-mentioned recessed portions are formed in nozzle connecting portions at the distal end constituent portion of the distal end of the insertion section 31 and pipe abutments formed at the respective portions of the distal end constituent portion in the endoscope 30, as shown in FIG. 34. More specifically, a main body 183 of the distal end constituent portion 188 is connected to a connecting pipe 169 for connecting a tube 168 and the main body 183. The main body 183 is also connected to a nozzle protective tube 166 fitted on the nozzle 39. For this reason, recessed portions 178 and 179 are present between the main body 183 and the connecting pipe 169 and between the main body 183 and the nozzle protective tube 166, respectively. It is, of course, difficult to cause the cleaning solution to contact the recessed portions 178 and 179 and obtain a desired flow speed enough to perform satisfactory cleaning in the recessed portions 178 and 179. A countermeasure against the recessed portions 178 and 179 will be described below.

Figure 35:
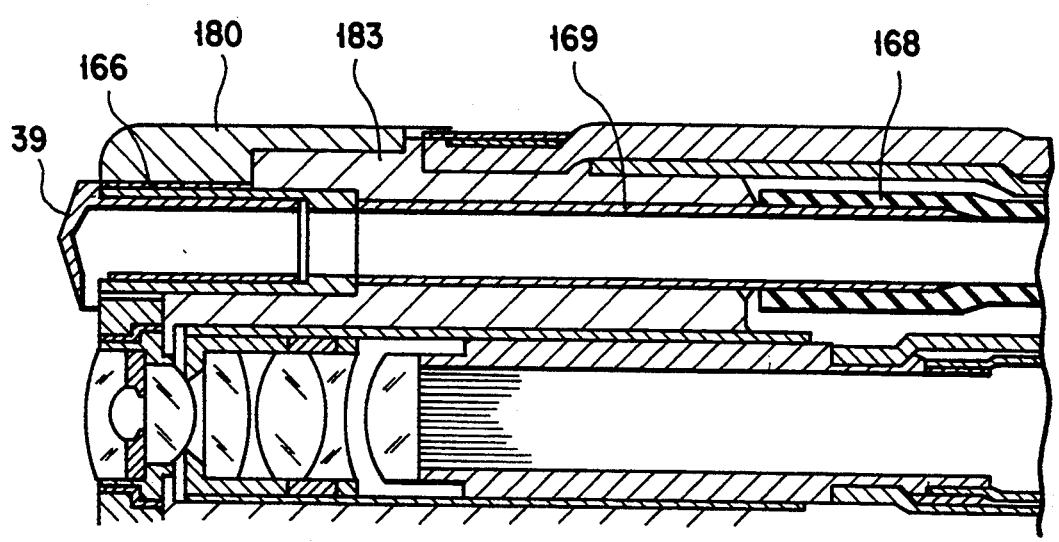
FIG. 35 is a sectional view showing a first modification of the properly improved conduit connecting portion at the distal end portion of the endoscope.

Referring to FIG. 35, the nozzle protective tube 166 is fitted on the nozzle 39 to insulate the nozzle 39. The nozzle protective tube 166 is fitted in the main body 183 of the distal end constituent portion of the endoscope 30. A distal end cover 180 is fixed to the main body 183 of the distal end constituent portion to insulate the main body 183 from a body wall. The tube 168 forms the first air supply conduit 37a. The tube 168 abuts against the connecting pipe 169 for connecting the tube 168 and the main body 183 of the distal end constituent portion. The nozzle protective tube 166 abuts against the pipe 169. The recessed portions 178 and 179 conventionally formed between the main body 183 of the distal end constituent portion and the nozzle protective tube 166 and between the main body 183 of the distal end constituent portion and the pipe 169 can be reduced into one. This remaining one recessed portion can be eliminated by adjusting the angle of the end face of the pipe 169 and the angle of the abutment portion of the nozzle protective pipe 166. In this case, the joint between the pipe 169 and the nozzle protective tube 166 becomes smooth to increase the cleaning power.

When a hole is formed in a material such as a metal or resin, a tapered portion 187 having the same angle as the included angle of a drill is formed at the inner edge of the hole, as shown in FIG. 34. When a tubular member such as the pipe 169 or the nozzle protective tube 166 is fitted in such a hole, the recessed portion 178 or 179 is formed at the tapered portion 187. A countermeasure against the tapered portion 187 will be described with reference to FIG. 36.

Figure 36:
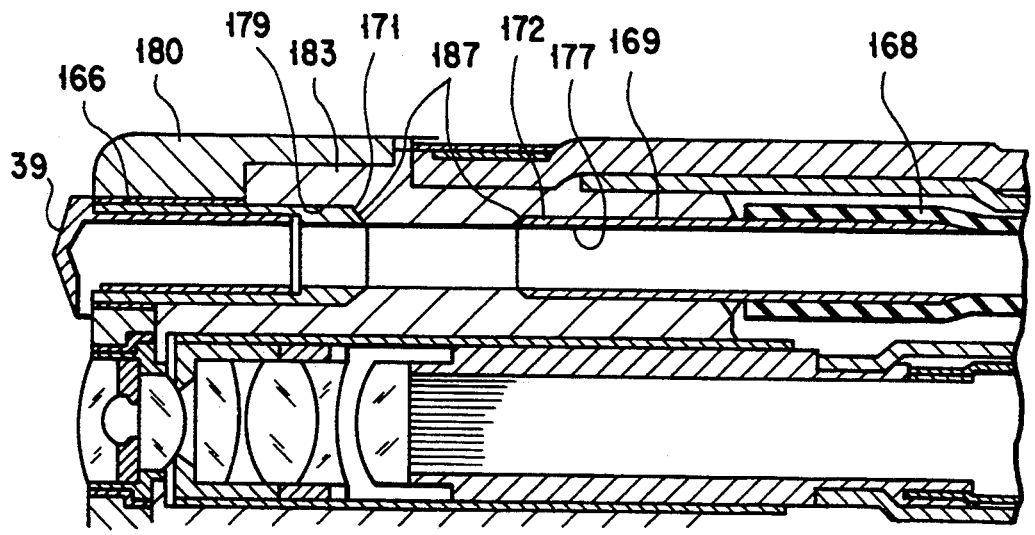
FIG. 36 is a sectional view showing a second modification of the properly improved conduit connecting portion at the distal end portion of the endoscope.

As shown in FIG. 36, a nozzle protective tube fitting hole 179 having a tapered portion cut at the same angle as the included angle of the drill and a pipe fitting hole 177 having the same arrangement are formed in the main body 183 of the distal end constituent portion. The nozzle protective tube 166 fitted on the nozzle 39 is fitted in the nozzle protective tube fitting hole 179. The pipe 169 connected to the tube 168 is fitted in the pipe fitting hole 177. The distal end portion of the nozzle protective tube 166 is a tapered portion 171 having the same taper angle as that of the tapered portion 187. The distal end portion of the pipe 172 has a tapered portion 172 having the same taper angle as that of the tapered portion 187. In this structure, the tapered portions 187 are canceled by the tapered end portions 171 and 172 of the connecting tubes 169 and 166 to form flat inner conduit surfaces free from recessed portions.

In the above embodiment, the structure of the distal end constituent portion 188 is exemplified. However, such a structure can also be applied to conduit connecting structures of the cylinders 51 and 52 and the connector 45 in the operation section 32.

Figure 37:
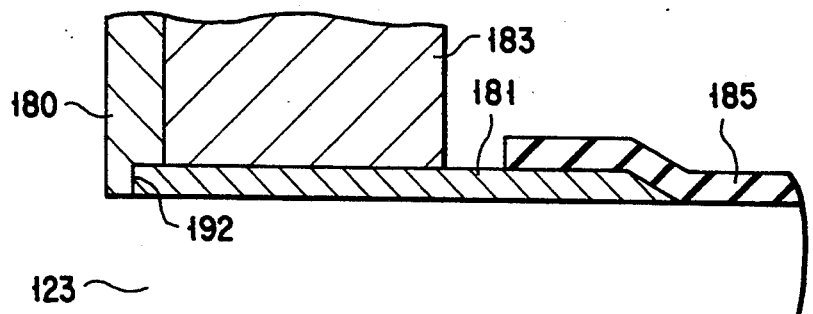
FIG. 37 is a sectional view showing a third modification of the properly improved conduit connecting portion at the distal end portion of the endoscope.

The conduit structure near the suction port 123 is shown in FIG. 37. The distal end cover 180 is mounted on the main body 183 of the distal end constituent portion to insulate the main body 183 from a body wall. A pipe 181 connected to a tube 185 forming the first suction conduit 41a is fitted and fixed on the main body 183. The pipe 181 is connected to the tube 185 such that the pipe 181 abuts against the end face of a stepped portion 192 formed on the inner edge of the distal end cover 180.

Figure 38:
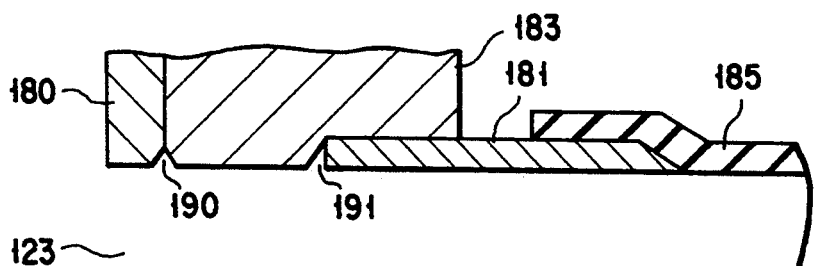
FIG. 38 is a sectional view showing part of a conventional conduit connecting portion at the distal end portion of the endoscope.

As shown in FIG. 38, recessed portions 190 and 191 as conduit joints are conventionally formed between the pipe 181 and the main body 183 of the distal end constituent portion and between the distal end cover 180 and the main body 183 of the distal end constituent portion. However, in the structure shown in FIG. 37, the number of conduit joints becomes one. In addition, since the end face of the pipe 181 matches the end face of the stepped portion 192 of the distal end cover 180, the joint is constituted by almost a flat surface, thereby increasing the cleaning power.

As described above, cleaning is performed by a control unit (not shown) in the following manner while cleaning tubes 19 and 142 are kept connected to the air/water supply cylinder 52 and the insertion port 43. This operation will be described with reference to FIG. 4. Cleaning water is stored in the cleaning tank 4. That is, the water supply valve 2 is opened to pour tap water from the faucet 1 to the cleaning tank 4. In this case, the valve 8 is opened as needed to mix a detergent. When cleaning water is sufficiently stored in the cleaning tank 4, the outer surface cleaning pump 11 and the conduit cleaning pump 14 are operated. The cleaning water stored in the cleaning tank 4 is supplied to the plurality of nozzles 13 of the cleaning tank 4 through the outer surface cleaning solution conduit 12. The cleaning solution is sprayed from each nozzle 13 to the outer surface of the endoscope 30. At the same time, the cleaning solution is injected in the conduits in the endoscope 30 through the conduit cleaning solution supply path 15 and the cleaning tube 19. Therefore, the outer surface and interior of each conduit in the endoscope 30 can be cleaned.

The conduit cleaning pump 14 has a delivery capacity (i.e., the delivery capacity for injecting the cleaning solution at a total of 3.5 (l/min) or more) for injecting the cleaning solution at a flow speed corresponding to the Reynolds number Re=3,387 or more. The interior of each conduit can be satisfactorily cleaned. In this case, the larger the pump capacity is, the higher the flow speed is in each conduit, and particularly a thin conduit. A pump of 0.5 kg/cm$^2$ to 4 kg/cm$^2$ can be preferably used in consideration of durability of the endoscope 30. More preferably, as described above, a pump of 2.15 kg/cm$^2$ or more is used. The conduit cleaning pump 14 can be continuously operated during cleaning to obtain a sufficient cleaning effect. However, as shown in FIG. 25, the pump 14 may be alternately operated for solution supply and suction. As shown in FIG. 26, the pump 14 can be intermittently operated. In this case, in addition to removal of the filth at a high flow speed, the filth can be dissolved in the cleaning solution, thereby providing efficient cleaning.

When the above cleaning process is completed, the discharge valve 27 is opened, and the discharge pump 28 is operated. In addition, the air pump 21 is operated to supply air to the conduits in the endoscope, thereby discharging the residual water.

A disinfection process is then started. The valve 7 is opened, and a disinfectant in the disinfectant tank 5 is injected in the cleaning tank 4. The outer surface cleaning pump 11 and the conduit cleaning pump 14 are then operated to supply the disinfectant to the outer surface and the interior of each conduit as in the cleaning water in the cleaning process, thereby disinfecting the respective components. Since the conduit cleaning pump 14 has the large capacity described above, the corners of the conduits can be satisfactorily disinfected, and a portion without disinfection will not be left.

When this disinfection process is completed, a discharge process is performed as in the cleaning solution in the cleaning process. When the discharge process is then completed, a rinsing process is started. In this rinsing process, the water supply valve 2 is opened to store tap water in the cleaning tank 4. As in the cleaning process, rinsing water is supplied to the outer surface and the interior of each conduit of the endoscope 30 to remove the disinfectant. The rinsing process is preferably repeated twice or the like in consideration of the presence of the residual disinfectant. The cleaning and disinfection processes of the endoscope 30 are completed.

As described above, in the endoscope system of this embodiment, the conduit cleaning pump 14 has a capacity having a delivery rate of 3.5 (l/min) or more and a delivery pressure of 2.15 (kg/cm$^2$), and the internal conduits of the endoscope 30 are formed to have a conduit structure capable of maintaining the cleaning effect of the cleaning solution flowed by means of this capacity. Therefore, all the internal conduits of the endoscope 30 can be satisfactorily cleaned.

FIGS. 39 and 40 show the second embodiment of the present invention. An endoscope system of the second embodiment comprises a cleaning apparatus for cleaning only the internal conduits in an endoscope 30. Referring to FIG. 39, reference numeral 100 denotes a conduit cleaning pump. This pump 100 has a capacity for a delivery rate of 3.0 (l/min) or more. A cleaning tube 101 connected to an air/water supply cylinder 52 and an insertion port 43 in the endoscope 30 is connected to the delivery port of the pump 100. A suction conduit 102 is connected to the suction side of the pump 100. The suction conduit 102 is connected to a cleaning solution suction conduit 104 through a first electromagnetic valve 103 and to a rinsing water suction conduit 106 through a second electromagnetic valve 105. The cleaning solution suction conduit 104 communicates with a cleaning water tank 107, and the rinsing water suction conduit 106 communicates with a rinsing water tank 108. The first electromagnetic valve 103, the second electromagnetic valve 105, and the conduit cleaning pump 100 are controlled by a control unit 109.

Cleaning water is stored in the cleaning water tank 107, and a disinfectant is stored in the rinsing water tank 108. Proteins are generally mixed in a body fluid. Since proteins coagulate upon contact with an acid, acidic water cannot be used as cleaning water. In this embodiment, for example, alkaline or neutral cleaning water is used as a cleaning solution.

Acidic ionized water has high disinfecting properties. In this embodiment, electrolysis of water using a water electrolysis unit 110 is performed to obtain alkaline ionized water serving as cleaning water and acidic ionized water serving as a disinfectant. The water electrolysis unit 193 shown in FIG. 40 has an alkaline ionized water discharge conduit 191 communicating with the cleaning water tank 107 and an acidic ionized water discharge conduit 192 communicating with the rinsing water tank 108.

Cleaning using this cleaning apparatus is performed as follows. The conduit cleaning pump 100 is driven to open the first electromagnetic valve 103, thereby supplying the cleaning water in the conduits. The first electromagnetic valve 103 is closed, and the second electromagnetic valve 105 is opened to perform a process serving as both the rinsing and disinfection processes in the conduits.

A commercially available disinfectant may be mixed in tap water containing a detergent or the disinfectant in the cleaning water tank 108. In this case, a rinsing process with cleaning water again may be preferably added after the disinfection process. Even in this cleaning apparatus, since the cleaning solution can be supplied to each conduit in the endoscope 30 at a flow speed corresponding to Re=3,387 or more, the interior of each conduit can be satisfactorily cleaned. In addition, the alkaline cleaning solution is used as the cleaning water to further increase the cleaning power.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An endoscope system comprising:
   an endoscope having internal conduits;
   a cleaning solution supply section formed inside said endoscope and communicating with said internal conduits;
   solution feed means for supplying a cleaning solution to said cleaning solution supply section; and
   flow regulate means for causing the cleaning solution, supplied from said cleaning solution supply section to said internal conduits by said solution feed means, to flow at a flow speed almost equal to a flow speed in said cleaning solution supply section in all flow paths of said internal conduits.

2. A system according to claim 1, wherein said solution feed means comprises a solution supply pump for supplying the cleaning solution at a delivery rate of not less than 3.0 (l/min) and at a delivery pressure of not less than 2.15 (kg/cm$^2$).

3. A system according to claim 1, wherein said solution feed means supplies an alkaline cleaning solution.

4. A system according to claim 1, wherein said internal conduits have a branch portion and a merging portion, and said flow regulate means comprises sectional area setting means for performing a setup such that a sum of sectional areas of upstream conduits, of all conduits branching from and merging into the branch and merging portions, which receive the cleaning solution is set to be almost equal to a sum of sectional areas of downstream conduits branching from and merging into the branch and merging portions.

5. A system according to claim 1, wherein said internal conduits comprise two tubes connected to each other, and said flow regulate means comprises first stepped portion eliminating means for forming an end face of a first tube as one of said two tubes into a tapered end face and for bringing said tapered end face into contact with an inner surface of an end portion of a second tube as the other of said two tubes, thereby eliminating a stepped portion on a conduit inner surface at a connecting portion of said two tubes.

6. A system according to claim 5, wherein said two tubes have equal inner diameters.

7. A system according to claim 5, wherein said first stepped portion eliminating means comprises a press member, brought into contact with an outer surface of said end portion of said second tube, for pressing said inner surface of said end portion of said second tube against said tapered end face of said first tube.

8. A system according to claim 5, wherein at least one of said two tubes comprises an elastic portion, and said tapered end face is brought into elastic contact with said inner surface of said end portion of said second tube as the other of said two tubes.

9. A system according to claim 1, wherein said internal conduits comprise two tubes connected to each other, and said flow regulate means comprises second stepped portion eliminating means for filling a filler in a recessed portion formed on an inner surface of a connecting portion between said two tubes to eliminate a stepped portion formed on said inner surface of said connecting portion between said two tubes.

10. A system according to claim 1, wherein said internal conduits comprise a stainless steel pipe, and further comprising polishing means for chemically polishing an inner surface of said stainless steel pipe to form a smooth inner surface.

11. A system according to claim 1, wherein said internal conduits comprise a bent portion, and said flow regulate means comprises means for forming an oval cross-section of said bent portion.

12. A system according to claim 1, wherein said internal conduits comprise a connecting portion formed such that an end face of a pipe abuts against an inner end face of a fitting hole of a main body of said endoscope, and said pipe is fitted in said fitting hole, and said flow regulate means comprises third stepped portion eliminating means for performing a setup such that an inclination angle of said end face of said pipe is set to be equal to an inclination angle of said inner end face of the fitting hole, thereby eliminating a stepped portion on an inner surface of said connecting portion.

13. An endoscope system comprising:
an endoscope having internal conduits;
a cleaning solution supply section formed inside said endoscope and communicating with said internal conduits;
solution feed means for supplying a cleaning solution to said cleaning solution supply section at a delivery rate of not less than 3.0 (l/min) and a delivery pressure of not less than 2.15 (kg/cm$^2$); and
flow regulate means for causing the cleaning solution, supplied from said cleaning solution supply section to said internal conduits by said solution feed means, to flow at a flow speed almost equal to a flow speed in said cleaning solution supply section in all flow paths of said internal conduits.

14. A system according to claim 13, wherein said internal conduits have a branch portion and a merging portion, and said flow regulate means comprises sectional area setting means for performing a setup such that a sum of sectional areas of upstream conduits, of all conduits branching from and merging into the branch and merging portions, which receive the cleaning solution is set to be almost equal to a sum of sectional areas of downstream conduits branching from and merging into the branch and merging portions.

15. A system according to claim 13, wherein said internal conduits comprise two tubes connected to each other, and said flow regulate means comprises first stepped portion eliminating means for forming an end face of a first tube as one of said two tubes into a tapered end face and for bringing said tapered end face into contact with an inner surface of an end portion of a second tube as the other of said two tubes, thereby eliminating a stepped portion on a conduit inner surface at a connecting portion of said two tubes.

16. A system according to claim 15, wherein said two tubes have equal inner diameters.

17. A system according to claim 15, wherein said first stepped portion eliminating means comprises a press member, brought into contact with an outer surface of said end portion of said second tube, for pressing said inner surface of said end portion of said second tube against said tapered end face of said first tube.

18. A system according to claim 15, wherein at least one of said two tubes comprises an elastic portion, and said tapered end face is brought into elastic contact with said inner surface of said end portion of said second tube as the other of said two tubes.

19. A system according to claim 13, wherein said internal conduits comprise two tubes connected to each other, and said flow regulate means comprises second stepped portion eliminating means for filling a filler in a recessed portion formed on an inner surface of a connecting portion between said two tubes to eliminate a stepped portion formed on said inner surface of said connecting portion between said two tubes.

20. A system according to claim 13, wherein said internal conduits comprise a stainless steel pipe, and further comprising polishing means for chemically polishing an inner surface of said stainless steel pipe to form a smooth inner surface.

21. A system according to claim 13, wherein said internal conduits comprise a bent portion, and said flow regulate means comprises means for forming an oval cross-section of said bent portion.

22. A system according to claim 13, wherein said internal conduits comprise a connecting portion formed such that an end face of a pipe abuts against an inner end face of a fitting hole of a main body of said endoscope, and said pipe is fitted in said fitting hole, and said flow regulate means comprises third stepped portion eliminating means for performing a setup such that an inclination angle of said end face of said pipe is set to be equal to an inclination angle of said inner end face of the fitting hole, thereby eliminating a stepped portion on an inner surface of said connecting portion.

* * * * *